United States Patent
Cohen et al.

(10) Patent No.: US 12,245,808 B1
(45) Date of Patent: Mar. 11, 2025

(54) LASER SURGICAL DEVICE

(71) Applicant: Memic Innovative Surgery Ltd., Or-Yehuda (IL)

(72) Inventors: Dvir Cohen, Ramot-Menashe (IL); Yaron Levinson, Tel-Aviv (IL)

(73) Assignee: Momentis Surgical Ltd., Or-Yehuda (IL)

( * ) Notice: Subject to any disclaimer, the term of this patent is extended or adjusted under 35 U.S.C. 154(b) by 498 days.

(21) Appl. No.: 16/511,017

(22) Filed: Jul. 15, 2019

Related U.S. Application Data

(60) Provisional application No. 62/698,171, filed on Jul. 15, 2018.

(51) Int. Cl.
| | |
|---|---|
| *A61B 18/24* | (2006.01) |
| *A61B 34/00* | (2016.01) |
| *A61B 90/50* | (2016.01) |
| A61B 17/00 | (2006.01) |
| A61B 17/295 | (2006.01) |
| A61B 18/00 | (2006.01) |
| A61B 34/20 | (2016.01) |
| A61M 25/01 | (2006.01) |

(52) U.S. Cl.
CPC .............. *A61B 18/24* (2013.01); *A61B 34/25* (2016.02); *A61B 90/50* (2016.02); *A61B 2017/00119* (2013.01); *A61B 2017/00314* (2013.01); *A61B 17/295* (2013.01); *A61B 2018/00666* (2013.01); *A61B 2018/00708* (2013.01); *A61B 2034/2061* (2016.02); *A61M 25/0116* (2013.01)

(58) Field of Classification Search
CPC ......... A61B 18/24; A61B 34/25; A61B 34/30; A61B 2034/301; A61B 2034/302; A61B 2034/303; A61B 2034/304; A61B 2034/305; A61B 2034/306; A61B 34/32; A61B 34/35; A61B 90/50; A61B 2034/2046; A61B 2034/2048; A61B 2034/2051; A61B 2034/2053; A61B 2034/2055; A61B 2034/2057; A61B 2034/2059; A61B 2034/2061; A61B 2034/2063; A61B 2034/2065; A61B 17/295; A61B 2017/00115; A61B 2017/00119; A61B 2017/00123; A61B 2017/00128; A61B 2017/00314; A61B 2018/00666; A61B 2018/00672; A61B 2018/00678; A61B 2018/00708; A61M 25/0116
USPC ......................................................... 606/15
See application file for complete search history.

(56) References Cited

U.S. PATENT DOCUMENTS

| | | | |
|---|---|---|---|
| 7,766,821 B2 | 8/2010 | Brunnen et al. | |
| 2009/0137952 A1* | 5/2009 | Ramamurthy | A61B 8/48 604/95.01 |
| 2017/0303824 A1* | 10/2017 | Schlesinger | A61B 1/018 |

(Continued)

*Primary Examiner* — Aaron F Roane
(74) *Attorney, Agent, or Firm* — Organization

(57) ABSTRACT

A surgical system including: a surgical mechanical arm including a plurality of sequentially coupled independently bendable flexible portions and terminating in a laser tool; a waveguide supplying laser light to the laser tool, where the waveguide follows a contour of the surgical mechanical arm; circuitry configured to: receive data regarding curvature of one or both of: the waveguide; one or more of the plurality of sequentially coupled independently bendable flexible portions; and perform one or more action based on the received data.

20 Claims, 15 Drawing Sheets

(56) References Cited

U.S. PATENT DOCUMENTS

2018/0188080 A1\* 7/2018 Waisman ............... A61B 18/24
2019/0053861 A1\* 2/2019 Lwin ..................... A61B 1/126

\* cited by examiner

LASER SURGICAL DEVICE

RELATED APPLICATIONS

This application claims the benefit of priority under 35 USC § 119(e) of U.S. Provisional Patent Application No. 62/698,171 filed Jul. 15, 2018, the contents of which are incorporated by reference as if fully set forth herein in their entirety.

This application is also related to U.S. Provisional Patent Application No. 62/686,023 filed Jun. 17, 2018 which has turned into PCT Application No. IL2019/050671 filed Jun. 13, 2019, U.S. patent application Ser. No. 15/915,292 filed Mar. 8, 2018 and U.S. patent application Ser. No. 15/916,302 filed Mar. 9, 2018.

The contents of the above applications are all incorporated by reference as if fully set forth herein in their entirety.

FIELD AND BACKGROUND OF THE INVENTION

The present invention, in some embodiments thereof, relates to a surgical laser tool and, more particularly, but not exclusively, to manipulation of a surgical laser tool using a surgical mechanical arm.

SUMMARY OF THE INVENTION

Example 1. A surgical system comprising:
a. a surgical mechanical arm comprising a plurality of sequentially coupled independently bendable flexible portions and terminating in a laser tool;
b. a waveguide supplying laser light to said laser tool, where said waveguide follows a contour of said surgical mechanical arm;
c. circuitry configured to:
  i. receive data regarding curvature of one or both of:
    said waveguide;
    one or more of said plurality of sequentially coupled independently bendable flexible portions; and
  ii. perform one or more action based on said received data.

Example 2. The surgical system according to Example 1, wherein said one or more action comprises:
generating a control signal; and
sending said control signal to at least one actuator controlling bending of one or more of said plurality of sequentially coupled independently bendable flexible portions.

Example 3. The surgical system according to any one of Examples 1-2, wherein said one or more action comprises:
adjusting a control signal; and
sending said control signal to at least one actuator controlling bending of one or more of said plurality of sequentially coupled independently bendable flexible portions.

Example 4. The surgical system according to any of Examples 1-3, wherein said one or more action comprises: adjusting at least one laser tool parameter.

Example 5. The surgical system according to Example 4, wherein said adjusting comprises adjusting one or more of laser wavelength, filter, laser intensity, laser pulse length.

Example 6. The surgical system according to any of Examples 1-5, wherein said one or more action comprises activating or deactivating lasing from said laser tool.

Example 7. The surgical system according to any one of Examples 1-6, wherein said system comprises one or more user interface;
wherein said one or more action comprises issuing an alert to a user through said one or more user interface.

Example 8. The surgical system according to any one of Examples 1-7, wherein said one or more action comprises activating or deactivating movement of said surgical mechanical arms.

Example 9. The surgical system according to any one of Examples 1-8, wherein said one or more action comprises generating an arm posture alternative.

Example 10. The surgical system according to any of Examples 1-9, wherein said data comprises input from at least one sensor.

Example 11. The surgical system according to Example 10, wherein said at least one sensor comprises one or more of:
one or more input device sensor; and
one or more sensor configured to measure curvature of one or more axial portion of said waveguide.

Example 12. The surgical system according to Example 11, wherein said sensor configured to measure curvature is a camera configured to collect images of at least a portion of said surgical mechanical arm.

Example 13. The surgical system according to any one of Example 1-12, wherein said circuitry is configured to compare said data regarding curvature with one or more threshold.

Example 14. The surgical system according to any of Examples 1-13, wherein said surgical mechanical arm comprises:
a first independently bendable flexible portion;
a second independently bendable flexible portion coupled to said first flexible portion;
wherein said waveguide follows a contour of said first independently bendable portion and said second independently bendable portion;
wherein said receiving comprises receiving data regarding curvature of said first independently bendable portion and said second independently bendable portion.

Example 15. The surgical system according to any of Examples 1-14, wherein one or more of said plurality of sequentially coupled independently bendable flexible portions is independently rotatable.

Example 16. The surgical system according to any of Examples 1-15, wherein each of said plurality of sequentially coupled independently bendable flexible portions is independently rotatable.

Example 17. The surgical system according to any of Examples 1-16, wherein said surgical mechanical arm includes a hollow passageway extending along a length of at least a portion of the surgical mechanical arm and said waveguide is housed within said hollow passageway.

Example 18. The surgical system according to Example 17, wherein said surgical mechanical arm includes at least one tubular structure, and said hollow passageway is within one of said at least one tubular structure.

Example 19. The surgical system according to any of Examples 1-18, wherein said waveguide is coupled to an outer surface of said surgical mechanical arm.

Example 20. The surgical system according to any of Examples 1-19, wherein said surgical mechanical arm comprises an additional tool.

Example 21. The surgical system according to Example 20, wherein said additional tool is configured to manipulate tissue.

Example 22. The surgical system according to Example 21, wherein said additional tool is a gripper.

Example 23. The surgical system according to any one of Example 20-22, wherein said additional tool comprises a monopolar electrosurgery tip.

Example 24. The surgical system according to any one of Examples 20-23, wherein said additional tool comprises a pair of bipolar electrosurgery contacts.

Example 25. The surgical system according to any one of Example 1-24, comprising a second surgical mechanical arm comprising a plurality of sequentially coupled independently bendable flexible portions and terminating in a second arm tool.

Example 26. The surgical system according to Example 25, wherein said second arm tool is a tool configured to manipulate tissue.

Example 27. The surgical system according to Example 26, wherein said second arm tool is a gripper.

Example 28. The surgical system according to any one of Example 25-27, wherein said second arm tool comprises a monopolar electrosurgery tip.

Example 29. The surgical system according to any one of Examples 25-28, wherein said second arm tool comprises a pair of bipolar electrosurgery contacts.

Example 30. A method of laser tool control comprising:
receiving data regarding curvature of one or more axial portion of a laser cable supplying laser light to a laser tool; and
generating a control signal for control of curvature of said one or more portion of said laser cable, based on said data.

Example 31. The method according to Example 30 comprises comparing said data with at least one threshold.

Example 32. The method according to Example 31, wherein said at least one threshold comprises one or more of; a damage threshold, a leakage threshold, a performance threshold.

Example 33. The method according to Example 32, comprising performing an action when one or more threshold is breached.

Example 34. A method of laser treatment comprising:
directing a laser tool to a region of a treatment site including at least one treatment area while monitoring curvature of one or more axial portion of a laser waveguide supplying laser light to said laser tool;
orientating said laser tool so that laser light is directed towards said at least one treatment area; and
lasing using said laser tool, while monitoring curvature of one or more axial portion of said laser waveguide.

Example 35. The method according to Example 34, wherein said laser waveguide follows a contour of at least a portion of a surgical mechanical arm.

Example 36. The method according to Example 35, wherein said monitoring comprises monitoring curvature of one or more axial portion of said surgical mechanical arm.

Example 37. The method according to Example 36, wherein said monitoring comprises using control signals for movement of said surgical mechanical arm.

Example 38. The method according to any one of Examples 34-37, wherein said monitoring comprises collecting one or more image and estimating curvature of one or more axial portion of said laser waveguide from said one or more image.

Example 39. The method according to any one of Examples 34-38, wherein said monitoring comprises comparing one or more measured curvature with one or more threshold.

Example 40. The method according to Example 39, comprising performing one or more actions upon identifying a breach in said one or more threshold during said comparing.

Example 41. The method according to any one of Examples 35-40, wherein said orientating comprises retroflexing said surgical mechanical arm.

Example 42. The method according to any one of Examples 34-41, wherein said lasing comprises ablating target tissue.

Example 43. The method according to Example 42, wherein said target tissue is endometrium.

Example 44. The method according to any one of Examples 34-43, comprising manipulating tissue.

Example 45. The method according to any one of Examples 34-44, comprising electrosurgically treating tissue.

Following are examples of some embodiments of the invention. Features of one example may be combined with features of one or more other examples, unless expressly prohibited and form additional examples of some embodiments of the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
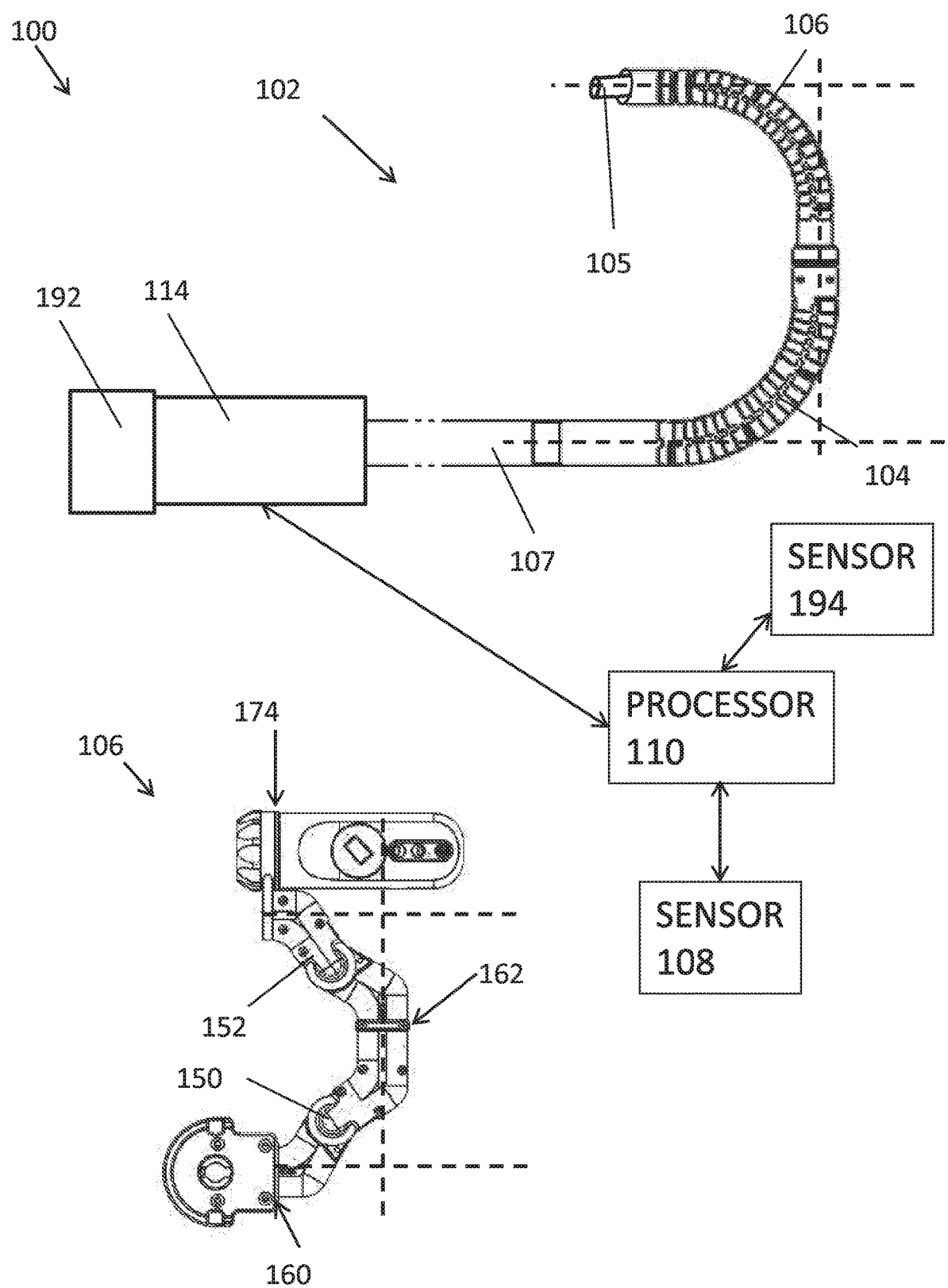
FIG. 1 is a simplified schematic of a surgical system including a laser device, according to some embodiments of the invention.

The present invention, in some embodiments thereof, relates to a surgical laser tool and, more particularly, but not exclusively, to manipulation of a surgical laser tool using a surgical mechanical arm.

Overview

A broad aspect of some embodiments of the invention relates to controlling a surgical laser using a surgical mechanical arm (also herein termed "arm") where a shape of a laser cable (e.g. including one or more laser waveguide) is controlled by a shape of the surgical mechanical arm. In some embodiments, the laser includes a laser cable and a laser tool where the laser cable supplies laser light to the laser tool.

In some embodiments, the laser waveguide follows a contour of the surgical mechanical arm, the shape of the laser waveguide being defined by the shape of the surgical mechanical arm. In some embodiments, the surgical mechanical arm includes a plurality of independently bendable flexible portions, bending of which changes the shape of the surgical mechanical arm. In some embodiments, the laser waveguide follows a contour of at least one of said bendable flexible portions and, in an exemplary embodiment, of all of said flexible portions.

In some embodiments, the laser cable is disposed within a hollow passageway of the surgical mechanical arm. For example, in some embodiments the surgical mechanical arm includes a tubular portion and the laser is disposed within a hollow passageway of the tubular portion. In some embodiments, the hollow passageway extends along the center of the tubular portion, for example along a central long axis of the tubular portion or along a portion thereof.

In some embodiments, the laser cable is connected to an outer surface (e.g. using a plurality of connectors and/or a sheath surrounding the laser cable and surgical mechanical arm) of the surgical mechanical arm, the attachment configured so that the laser follows an outer contour of the arm. In some embodiments, the laser tool is disposed at a distal end of the surgical mechanical arm.

An aspect of some embodiments of the invention relates to monitoring and/or controlling of curvature of flexible portion/s of the arm e.g. to control corresponding curvature of portion/s of the laser cable.

In some embodiments, control is based on signal/s received from one or more sensor. Some examples include: signals received from sensor/s directly sensing curvature of one or more axial portion of the laser cable and/or sensing curvature of the surgical mechanical arm (e.g. sensing curvature of one or more flexible portion and/or axial region/s of the laser cable which correspond with arm flexible portion/s); signals received from one or more sensor connected to the laser cable and/or one or more sensor connected to the surgical mechanical arm; Signals received in response to monitoring laser signals e.g. by identifying laser leakage; signals received using one or more optical sensor, e.g. a camera capturing image/s of the arm from which curvature is estimated.

Additionally or alternatively, in some embodiments, control is based on signal/s generated by user input/s e.g. from one or more sensor sensing user input for example, input device sensor/s where a user manipulates the input device to control movement and/or shape of the surgical mechanical device.

Additionally or alternatively, in some embodiments, control is based on actuation signal/s (e.g. recorded in a memory) and/or actuator control signal/s for control of actuators which manipulate the surgical mechanical arm.

A potential advantage of a flexible surgical mechanical arm including a laser tool is that, in some embodiments, treatment, using the arm including a laser tool, does not require contact between the tool and tissue to be treated. Treatment (e.g. laser cutting) which does not require contact, in some embodiments, reduces force on the tissue (e.g. as compared to manual cutting and/or electrosurgery) potentially reducing damage to tissue. Potentially, reduced force on tissue and/or the arm during treatment, in some embodiments, improves control of position of the arm and/or restriction of treatment to desired treatment area/s. In some cases, using traditional and/or electrosurgical cutting, where the surgical tool is placed in contact with (and/or in close proximity to) a treatment site, contact may move the tissue and moving the tool across tissue discontinuities may result in abrupt movement (e.g. "jumping" of the tool).

In some embodiments, curvature of the laser waveguide is monitored. In some embodiments, monitoring is to prevent high curvature (e.g. from movement of the surgical mechanical arm) where damage occurs to the laser waveguide. Alternatively or additionally, in some embodiments, monitoring is to prevent curvatures where there is leakage of laser light from the waveguide. Alternatively or additionally, in some embodiments, monitoring is to optimize laser performance.

In some embodiments, upon identifying curvature above a desired level (e.g. one or more threshold), one or more action is performed. Exemplary actions may include; disabling movement of the arm and/or lasing, changing a control signal to change the curvature of the arm, issuing one or more communication and/or alert to a user e.g. through user interface/s, generating and/or displaying to a user an arm posture alternative.

In an exemplary embodiment, a curvature approaching a breakage curvature is sensed and/or user control signals correspond to a curvature approaching the breakage curvature. In some embodiments, in response, one or more of the following occurs; an alert is issued; the control signals are adjusted before being sent to actuators.

In an exemplary embodiment, a curvature where laser efficiency is reduced by leakage is sensed (and/or user control signals correspond to this curvature). In some embodiments, in response, one or more of the following occurs; an alert is issued; the control signals are adjusted before being sent to actuators; lasing is disabled; and/or an alternative arm posture alternative where the laser tool is directed at the same target is presented to the user and/or is adopted by the arm.

In some embodiments, identifying desired and/or undesirable curvatures is by comparison to one or more threshold. In some embodiments, thresholds are dependent of duration of time at which the curvature is maintained. In some embodiments, identifying is, additionally or alternatively, using a look-up table.

In some embodiments, a surgical mechanical arm (e.g. including a laser tool) is configured to perform one or more automatic gesture and/or movement (e.g. includes circuitry configured to generate control signal/s for automatic gesture/s and/or automated movement). In some embodiments, a user selects and/or inputs an automatic gesture command at a user input.

In some embodiments, an automatic gesture includes repetitive movement. In some embodiments, a user performs a movement with the tool (e.g. laser tool) and then selects a number of times for the tool to perform the same gesture. In some embodiments, a user inputs a command to cut tissue (e.g. to a specified depth) and the surgical mechanical arm directs the tool (e.g. laser tool) to perform a cutting action (e.g. lasing back and/or forth across a cut line) repetitively until the desired cut is achieved.

In some embodiments, automated movement includes cutting (e.g. laser cutting) along a specified line and/or contour. In some embodiments, the line and/or contour is specified by a user e.g. by selecting using an anatomical mapping. In some embodiments, a line and/or contour is automatically generated by software e.g. software which includes an anatomical mapping. In some embodiments, automated movement includes selecting positioning of the arm and/or movements of the arm e.g. from a plurality of possibilities e.g. to prevent damage of tissue e.g. to maximize lasing efficiency from the arm and/or prevent leakage from and/or damage to the laser cable.

In some embodiments, one or more laser parameter is adjusted (e.g. automatically adjusted) based on actual movement (and/or projected movement e.g. based on control signal/s) of the laser and/or surgical mechanical arm. In some embodiments, actual movement is measured using one or more sensor. In some embodiments, when a user moves (and/or selects control to move) the laser rapidly, power and/or pulse length of the laser is automatically increased e.g. so that the laser continues to cut as opposed to just heating tissue.

In some embodiments, a surgical system includes a planning system where an approach of a surgical mechanical tool and/or posture of the tool at a surgical site and/or during treatment is automatically selected and/or recommended by circuitry. In some embodiments, anatomical mapping of a treatment area is used to provide topography of a working space for the surgical mechanical arm. In some embodiments, given one or more input parameter orientation, movements of the arm (optionally during treatment) are selected and/or recommended (e.g. by displaying option/s at a user interface). In some embodiments, input parameters include one or more of a given entry point and/or angle of the arm (e.g. defined by vaginal access), a treatment target, a treatment type (e.g. ablation and/or tissue removal). In some embodiments, entry angle and/or point of the arm is selected and/or recommended, for example, based on one or more input parameter.

In some embodiments, as referred to herein, performing one or more actions (e.g. via circuitry, such as via a system controller) may also involve limiting or preventing actions, e.g. disabling or stopping movement of the surgical arm, preventing lasing, and/or otherwise restricting operation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Surgical System

FIG. 1 is a simplified schematic of a surgical system 100 including a laser tool 105, according to some embodiments of the invention.

In some embodiments, system 100 includes a surgical mechanical arm 102.

In some embodiments, mechanical arm 102 includes a plurality of flexible portions. In some embodiments, the mechanical arm includes one or more rigid portion where, in some embodiments, flexible portions alternate and/or are coupled by rigid portions. In some embodiments, bending at one or more of the flexible portion is where bending is distributed along a length of the flexible portion.

In some embodiments, surgical mechanical arm 102 includes a first flexible portion 104 coupled to a second flexible portion 106, coupled to a laser tool 105. In some embodiments, a distal portion of the surgical mechanical arm (e.g. including portions 104, 106, 105) is coupled to a surgical mechanical arm support 107. In some embodiments, support 107 is rigid.

In some embodiments, a long axis length of support 107 is long, for example, with respect to a long axis length of other portion/s of the arm. In some embodiments, a long axis length of support 107 is 2-30 times, or 3-20, or 3-10, times, or at least 3 times, or larger or smaller or intermediate multiples or ranges of a long axis length of first flexible portion 104, second flexible portion 106 and a coupling portion coupling the flexible portions.

In some embodiments, a flexible portion length along its long axis is at least 2 times, at least 3 times, at least 4 times, at least 6 times a maximum extent of the flexible portion perpendicular to the long axis (e.g. a diameter of the flexible portion). In some embodiments, one or both flexible portions 104, 106 are bendable, each portion in a single bending plane. In some embodiments, each flexible portion is bendable in a single bending plane in one rotational direction from a straight configuration. In some embodiments, a long central axis of the flexible portion bends in one plane.

In some embodiments, freedom of movement of a device flexible portion is restricted, for example, to match an aspect of freedom of movement of a human arm. In some embodiments, one or more flexible portion (e.g. each flexible portion) is uni-directionally bendable.

In some embodiments, one or both flexible portions 104, 106, are rotatable about a flexible portion long axis. Rotation of first flexible portion 104 thereby changes an orientation of the single bending plane of second flexible portion 106.

In some embodiments, mechanical arm 102 is a surgical mechanical arm, for example, sized and/or shaped for insertion into a body (e.g. human body). In some embodiments, the surgical mechanical arm is sized and/or shaped for laparoscopic surgery and/or for insertion through a natural orifice and/or lumen e.g. vagina, anus, mouth, trachea, esophagus, ear canal. In some embodiments, a maximum cross sectional dimension of the arm and/or of a distal portion of the arm is less than 20 mm, less than 15 mm, less than 10 mm. In some embodiments, a maximum cross sectional dimension of the arm and/or of a distal portion of the arm is between 0.5-20 mm, or 1-10 mm, or 5-9 mm, or 1-5 mm, or lower or higher or intermediate ranges or dimensions. In some embodiments, the distal portion is defined as a distal 5-90%, or 5-50%, or 5-20%, or lower or higher or intermediate percentages or ranges of a long axis length of the mechanical arm and/or is defined as a portion of the arm distal of and including second flexible portion 106.

In some embodiments, surgical arm 102 is actuated by a motor unit 114. In some embodiments, surgical mechanical arm 102 is supplied with electrical power e.g. for electrosurgery through motor unit 114. In some embodiments, motor unit 114 receives electrosurgical power from an electrosurgical power generator (not illustrated).

In some embodiments, system 100 includes and/or is connected to a laser supply 192 where laser supply 192 supplies laser tool 105 with laser light e.g. where laser cable/s each cable including one or more waveguide (e.g. where one or more of the waveguides is an optical fiber) transfer laser light generated at supply 192 to tool 105. In some embodiments, laser supply 192 is located in proximity to motor unit 114 (e.g. coupled to and/or attached to motor unit 114). In some embodiments, laser supply 192 is connected to laser tool 105 by laser cable/s which, in some embodiments pass through motor unit 114. Optionally, laser cables pass through the surgical arm 102.

In some embodiments, system 100 includes an input unit or device, for example, an input arm 106. In some embodiments, the input arm includes a first flexion joint 150 and a second flexion joint 152.

In some embodiments, system 100 includes one or more sensor 108 which senses the position of one or more portion of input arm 106. In some embodiments, one or more sensor 108 measures movement between portion/s of the input device, for example, flexion at flexion joints 150 and/or rotation about rotational joint/s 160, 162, 174. Additionally or alternatively, in some embodiments, sensors 108 receive user inputs e.g. a user input to lase using a laser tool e.g. a user input to activate an electrosurgical tool.

In some embodiments, system 100 includes one or more sensor 194 which senses curvature and/or torque of portion/s of arm 102. In some embodiments, one or more sensors 194 are configured as a part of the motor unit of the surgical arm, for example on a rotating wheel or gear of the motor unit which actuates movement of one or more arm portions. In some embodiments, information on arm position is calculated based on sensors of the motor unit. In an example, arm position information is calculated in accordance with a length and/or amount of tension set to elongate elements which control movement of arm portions, such as flexion and/or rotation.

In some embodiments, sensor/s 194 include one or more sensor located on arm 102 (e.g. strain gauge e.g. contact sensor). In some embodiments, sensor/s 194 include one or more sensor located on the laser (optionally on the laser cable) and/or coupled to the laser and/or in proximity to the laser. In some embodiments, sensor/s 194 include one or more optical and/or heat sensor configured to detect leakage of laser light from a laser tool. Optionally, laser power loss is detected. In some embodiments, sensor/s 194 include one or more sensor within a treatment space (e.g. located within the abdominal cavity where system 100 is used during laparoscopic treatment). In some embodiments, sensor/s include one or more optical sensor (e.g. a camera where measurements e.g. curvature of portion/s of the arm and/or laser are extracted from collected image/s).

Figure 9:
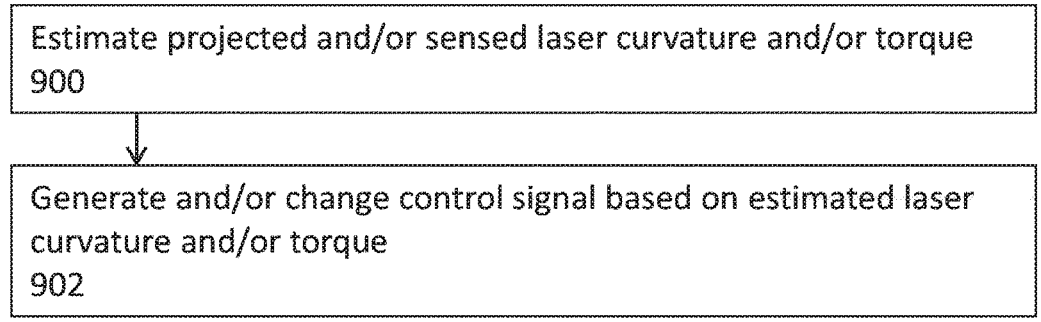
FIG. 9 is a flow chart of a method of laser tool control, according to some embodiments of the invention.
Figure 12:
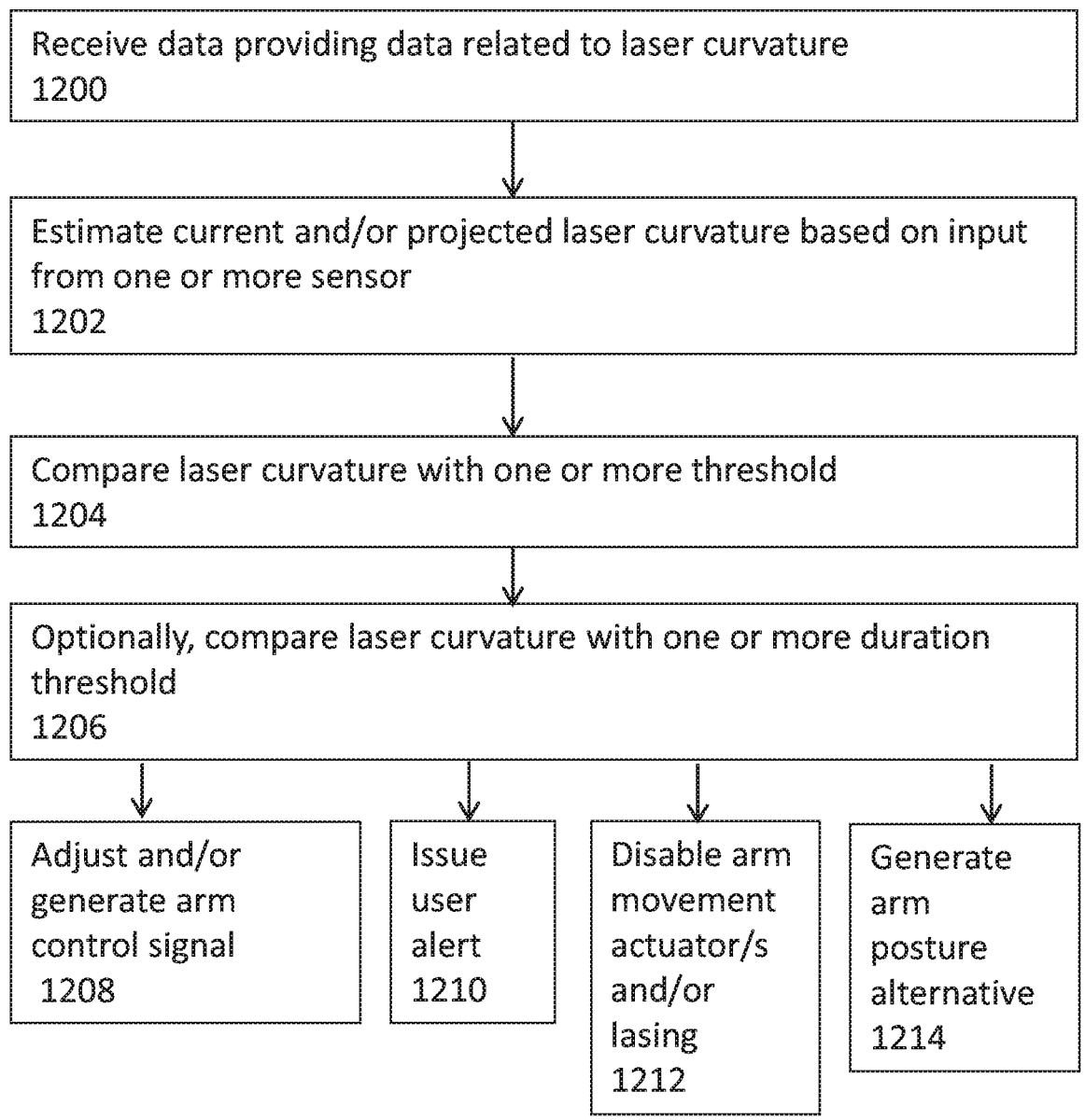
FIG. 12 is a flow chart of a method of laser treatment, according to some embodiments of the invention.

In some embodiments, system 100 includes a processor 110 which receives a signal from sensor/s 108 and/or sensor/s 194 and generates one or more control signal (e.g. including one or more feature as described regarding and/or illustrated in FIG. 9 and/or FIG. 12). Additional examples of control signals include signals that limit movement and/or modify a movement range; generating an alert that a range limit is being reached; suggesting an alternative route (e.g. an alternative bending angle), and/or other control signals.

In some embodiments, processor 110 sends the generated control signal to motor unit 114 which, in some embodiments, actuates movement of surgical mechanical arm 106, based on the control signal.

In some embodiments, the processor instructs the motor unit to move the surgical mechanical arm into a configuration where a shape of the surgical arm corresponds to a shape of the input arm, for example, where the surgical device has about the same angles between corresponding segments as the input device. In some embodiments, angles between segments are measured as intersections between central long axes of the arm at rotational joints, for example, as illustrated by dashed lines on FIG. 1.

Additional examples of systems including surgical arms and/or input devices such as input arms are for example as described in International Patent Application WO2016/035084, the contents of which are incorporated by reference.

Figure 2:
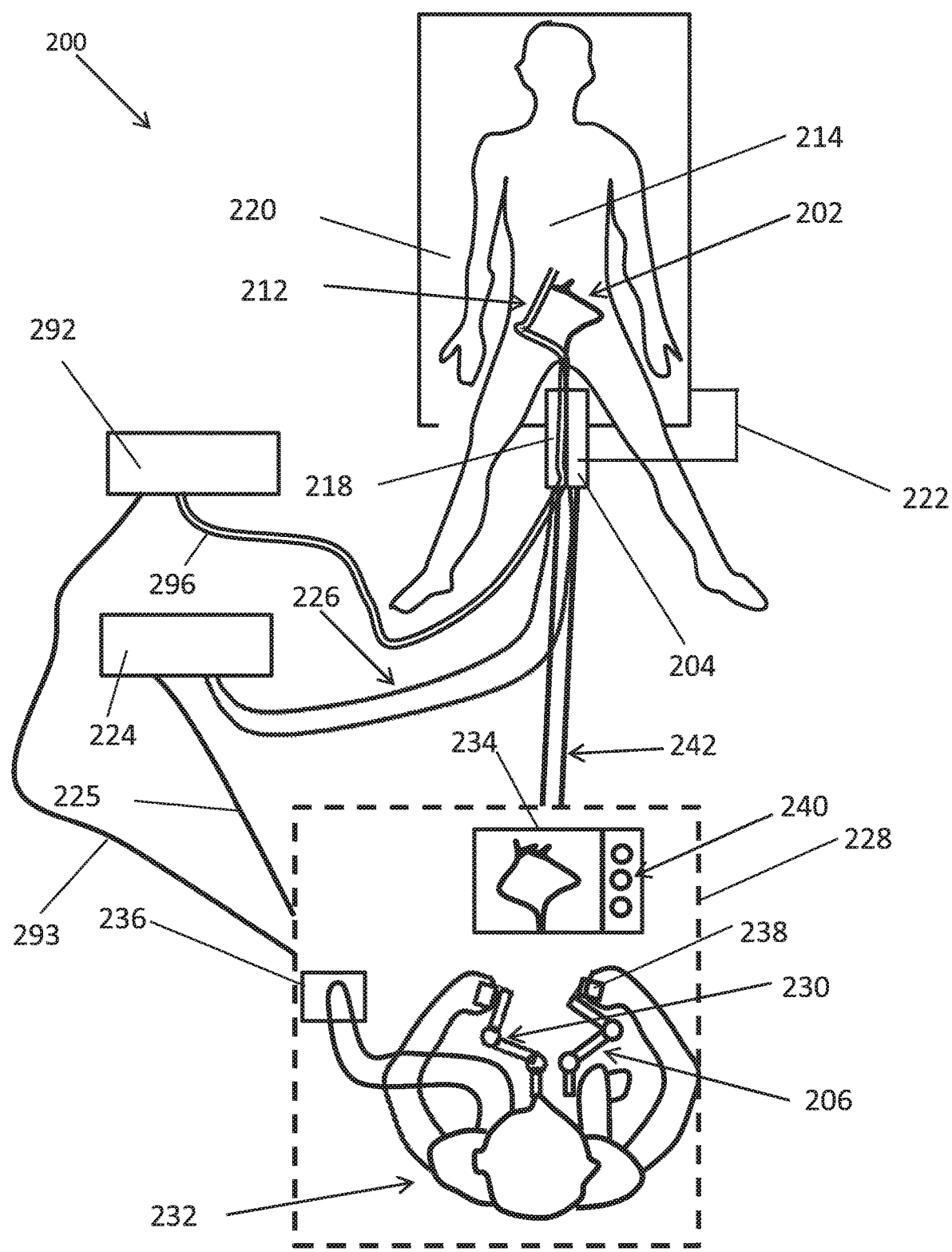
FIG. 2 is a simplified schematic of a surgical system including a laser device, according to some embodiments of the invention.

FIG. 2 is a simplified schematic of a surgical system 200 including a laser device, according to some embodiments of the invention.

In some embodiments, surgical system 200 includes at least one surgical mechanical arm, for example, a plurality of surgical mechanical arms 202, 212 e.g. two surgical mechanical arms. In some embodiments, surgical mechanical arms are sized and/or shaped for insertion into a human patient's body 214.

In some embodiments, a surgical mechanical arm 212 (or a plurality of surgical mechanical arms) includes one or more laser tool e.g. for example, including one or more feature as described regarding and/or illustrated in one or more of FIGS. 3, 4A-C, 6A-B, 7A-B, 8A-B.

In an exemplary surgical system, the system includes a first surgical mechanical arm 212 including a laser tool and a second surgical mechanical arm 202 including an electrosurgical tool.

In some embodiments, system 200 includes connectivity to and/or includes a laser supply 292 where, in some embodiments, laser supply 292 is configured to supply laser light suitable for performing surgery and/or treatments on tissue.

In some embodiments, surgical mechanical arm 212 includes a laser tool (or a plurality laser tool/s) which is connected to laser supply 292 by one or more laser cable.

In some embodiments, laser supply 292 supplies laser light to the laser tool. In some embodiments, laser supply 292 is a $CO_2$ or argon or potassium titanyl phosphate (KTP) laser supply, for example, an off the shelf laser supply such as Lumenis® AcuPulse™ DUO or UltraPulse® DUO laser supply. In some embodiments, laser supply 292 is connected to the laser tool (e.g. the laser tool comprised within surgical arm 212) by connection 296 which, in some embodiments, includes one or more laser cable. In some embodiments, laser supply 292 is connected to the laser tool by laser cable/s which, in some embodiments pass through motor unit 218.

In some embodiments, continuous waveguide/s extend from laser supply 292, to the laser tool. Optionally, the waveguide/s extend within connection 296. Alternatively, in some embodiments, laser cable/s extend from laser supply 292 and connect (e.g. at one or more socket) to the motor unit 218 and/or to surgical mechanical arm 212. In some embodiments, socket/s are compatible with more than one laser supply and/or laser cable. In some embodiments, motor unit 218 and/or surgical mechanical arm 212 includes sockets compatible with more than one laser supply and/or laser cable.

In some embodiments, the waveguide/s extend through motor unit 218 and/or through surgical mechanical arm 212 to the laser tool.

In some embodiments, laser supply 292 is connected by a data connection 293 (which, in some embodiments, is wireless, and in some embodiments, includes one or more cable) to control console 228.

In some embodiments, the system includes at least one motor unit, for example, a plurality of motor units 204, 218, where, in some embodiments, each of surgical mechanical arms 202, 212 is actuated by a motor unit. In some embodiments, a first surgical arm 202 is actuated by a first motor unit 204 and/or a second surgical arm 212 is actuated by a second motor unit 218.

In some embodiments, one or more motor unit and/or one or more surgical arm is attached to a patient support surface 220 (e.g. a bed), for example by a support 222. In an exemplary embodiment, one or more motor unit is attached to patient support surface 220. A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

In FIG. 2, patient 214 is illustrated in a suitable position for insertion of the device into and/or through the vagina (and/or anus and/or undercarriage), where, for example, the patient's legs are apart (e.g. elevated and/or held apart e.g. held by stirrups which are not illustrated).

In some embodiments, surgical arms 202, 212 are controlled (e.g. by a user 232) at a control console 228. In some embodiments, movement of surgical arms 202, 212 is controlled. In some embodiments, electrosurgical charging of arms 202, 212 is controlled. In some embodiments, actuation of arm tool/s (e.g. opening and/or closing of a gripper tool) is controlled. In some embodiment, lasing of laser tool/s is controlled.

In some embodiments, one or more motor unit (e.g. each motor unit 204, 218) is connected to control console via data and/or electrical supply connections 242.

In some embodiments, control console 228 includes a plurality of user interfaces:

In some embodiments, control console 228 includes one or more input arm 206, 230, where the control console is configured to generate control signals upon movement of the arm/s. In some embodiments, a processor (not illustrated) generates control signals when input arm/s are moved (e.g. as described regarding sensor 108 and processor 110, FIG. 1). In some embodiments, one or more input arm includes an additional user interface (not illustrated), for example, one or more button and/or switch.

In some embodiments, control console 228 includes one or more additional user interface 240 (e.g. button, switch) e.g. located on and/or near display 234.

In some embodiments, control console includes a display 234. In some embodiments, display 234 is configured to display imaging of a surgical zone, for example, to display images collected by a camera inserted into patient 214 e.g. with surgical arms 202, 212. In some embodiments, display 234 is a touch screen configured to receive user input, potentially providing a user input.

In some embodiments, a user controls lasing of one or more laser tool using the control console and/or one or more user interface on the control console. For example, in some embodiments, the user controls whether a laser tool lases or is inactive. In some embodiments, a user selects one or more laser parameter (e.g. through one or more user interface), for example, one or more of wavelength, a filter (e.g. from a plurality of filters) and laser intensity. In some embodiments, a user (e.g. user 232 and/or an additional user) controls laser tool/s using one or more control console user interface e.g. one or more of user interface 240, display 234, input arm/s 206, 230, foot pedal 236. Alternatively or additionally, in some embodiments, user 232 (and/or an additional user) controls laser tool/s and/or the laser supply through user input/s located at laser supply 292.

In some embodiments, the processor receiving laser control signal/s inputted by a user evaluates the signal/s (e.g. including one or more feature as illustrated in and/or described regarding FIG. 9 and/or FIG. 12).

In some embodiments, system 200 includes connectivity to and/or includes an electrosurgical generator 224. In some embodiments, for example, as known in the art of electrosurgery, electrosurgical generator 224 supplies high-frequency (e.g. radio frequency) alternating polarity electrical current. In some embodiments, electrosurgical generator 224 is configured to supply different frequencies and/or powers, for example, suitable for cutting and/or coagulating and/or desiccating and/or fulgurating tissue.

In some embodiments, electrosurgical generator 224 is a part of control console 228. Alternatively, in some embodiments, electrosurgical generator 224 is a separate device from the control console and/or from the motor units, which may include connectivity to any commercially available electrosurgical generator. For example, in an exemplary embodiment, electrosurgical generator 224 is a Covidien Force FX ESU Electrosurgical Generator. In some embodiments, supply to the motor units is via cable/s 226 which are, for example, configured to transfer radio frequency electrosurgical power.

In some embodiments, one or more surgical mechanical arm 202, 212 is supplied with electrical power by a motor unit to which the arm is attached. In some embodiments, surgical arm/s are supplied (e.g. indirectly through motor unit/s) with power by electrosurgical generator 224.

In some embodiments, electrosurgical generator 224 includes one or more user interface e.g. for control of supply of electrosurgical power supply to arms 202, 212. In some embodiments, the electrosurgical generator is controlled by a control console user interface e.g. 234 and/or 240.

In some embodiments, the control console includes a foot pedal 236. Alternatively or additionally, foot pedal 236 is provided as part of and/or attached to electrosurgical generator 224. In some embodiments, foot pedal 236 is connected via a data and/or power connection 225 to electrosurgical power generator 224. In some embodiments, foot pedal 236 controls supply of electrosurgical power to the surgical mechanical arm/s 202, 212.

In some embodiments, system 200 includes a processor (not illustrated) configured to receive signal/s from user input/s (e.g. one or more of input arm/s 206, 230, display 234, additional user interface/s 240, foot pedal 236). In some embodiments, the processor sends control signals to motor units 204, 218 and/or electrosurgical generator 224 e.g. based on signal/s received from user input/s.

In some embodiments, control console 228 includes a processor. Alternatively or additionally, in some embodiments, processing is hosted by an external processor which is, for example, configured to receive user input signal/s and/or send control signals to motor unit/s and/or the electrosurgical generator.

In some embodiments, foot pedal 236 and/or electrosurgical generator 224 include a processor configured to generate control signals (e.g. based on sensed pressure of user 232 pressing on portion/s of foot pedal 236). In some embodiments, electrical power supplied to motor units is varied based on the control signals. In some embodiments, foot pedal control signals do not pass through a control console processor.

In some embodiments, laser supply 292 includes an internal processor which is, in some embodiments, configured to generate control signals (e.g. based on sensor input and/or user interface input).

In some embodiments, a first input arm 206 controls movement of first surgical arm 202 and/or a second input arm 230 controls movement of second surgical arm 212. In some embodiments, a user positions and/or moves an input arm 206 by grasping an input arm handle 238.

In some embodiments, system 200 includes an electrosurgical switching unit, for example, connected between electrosurgical generator 224 and motor units 204, 218 which, for example, switches electrosurgical power supply (e.g. on and/or off) from the electrosurgical generator, for example, upon receiving a signal (e.g. from an electrosurgical switching unit user interface and/or from an external processor).

In some embodiments, system 200 includes a laser switching unit, for example, connected between laser supply 292 and a laser tool (which is part of arm 212) which, for example, switches laser light supply (e.g. on and/or off) from the laser supply, for example, upon receiving a signal (e.g. from a processor).

Figure 3:
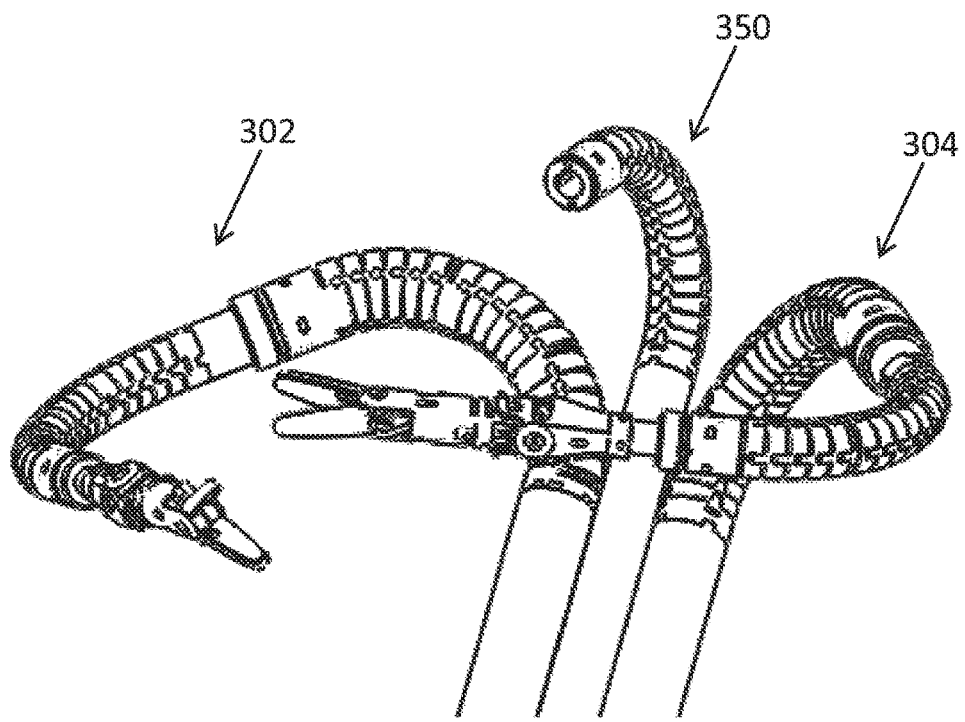
FIG. 3 is a simplified schematic of a surgical device including a laser device, according to some embodiments of the invention.

FIG. 3 is a simplified schematic of a surgical device including a laser device, according to some embodiments of the invention.

In some embodiments, a surgical system includes more than one surgical mechanical arm. In some embodiments, one or more arm (e.g. a first and a second surgical mechanical arm 302, 304 respectively) are inserted with one or more surgical mechanical lasing arm including a laser tool 350. In some embodiments, one or more surgical arm includes electrosurgical tool/s and/or tissue manipulation tools. In some embodiments, lasing arm 350 has more or less articulations than other surgical mechanical arm/s of the system.

Exemplary Surgical Mechanical Arms Including Exemplary Laser Tools

Figure 4A:
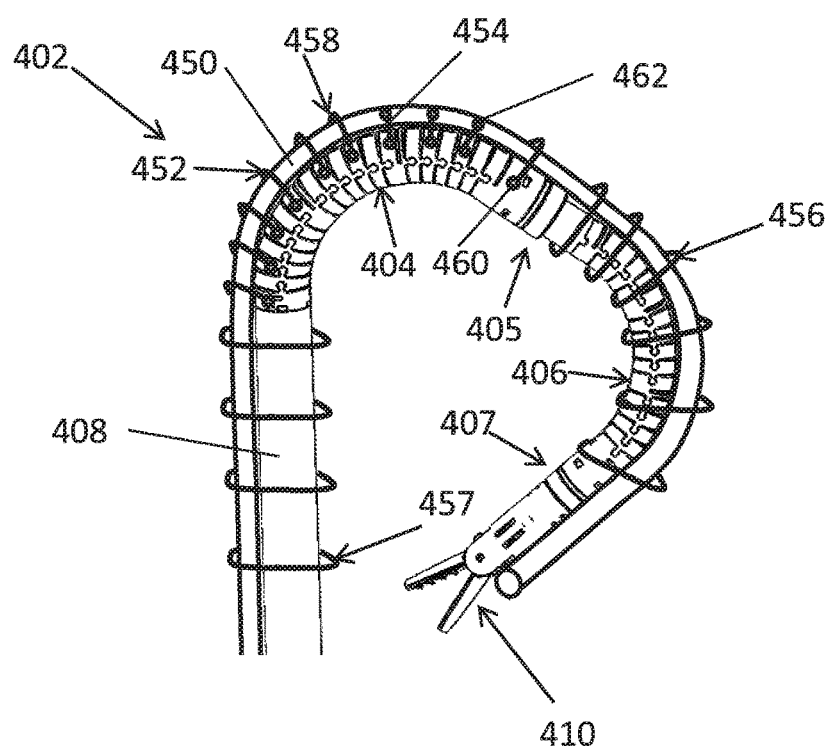
FIG. 4A is a simplified schematic of a surgical mechanical arm including a laser device, according to some embodiments of the invention.

FIG. 4A is a simplified schematic of a surgical mechanical arm 402 including a laser device 450, according to some embodiments of the invention.

In some embodiments, surgical mechanical arm 402 includes one or more feature as illustrated and/or described regarding surgical mechanical arm 102 FIG. 1 and/or surgical mechanical arm 212 FIG. 2.

In some embodiments, a surgical laser 450 (e.g. a laser cable) is coupled and/or attached to surgical mechanical arm 402 so that at least a distal portion of the surgical laser 450 (e.g. of the laser cable) follows a contour of arm 402. In some embodiments, surgical laser 450 is attached to arm 402 using a plurality of connectors 452, 454, 456.

In some embodiments, a single type of connector couples laser 450 to the surgical mechanical arm. Alternatively, more than one type of connector is used, for example, where different types of connector 452, 454, 456, 457, 458 connect different axial regions of the mechanical arm to laser 450 (e.g. as illustrated in FIG. 4A). Alternatively, different types of connector are used in the same axial region of the arm, e.g. different types of connectors being used to connect a flexible portion to the laser.

In some embodiments, one or more connector e.g. connectors 452, 454, 458 extends around a portion of a circumference of an axial portion of the arm and/or laser.

In some embodiments, one or more connector extends around an entire circumference of the arm and/or laser.

In some embodiments, one or more connector e.g. connectors 456, 457 extends around a circumference encompassing both the arm and laser.

In some embodiments, one or more connector is fixed to a portion of the arm (e.g. welded and/or glued onto the arm), where, in some embodiments, a fixation between a connector and the arm is illustrated by a circle e.g. fixed point 460. Alternatively or additionally, in some embodiments, one or more connector is fixed to a portion of the laser (e.g. welded and/or glued onto the laser). In some embodiments, a fixation between a connector and the laser is illustrated by a circle e.g. fixed point 462.

Figure 4B:
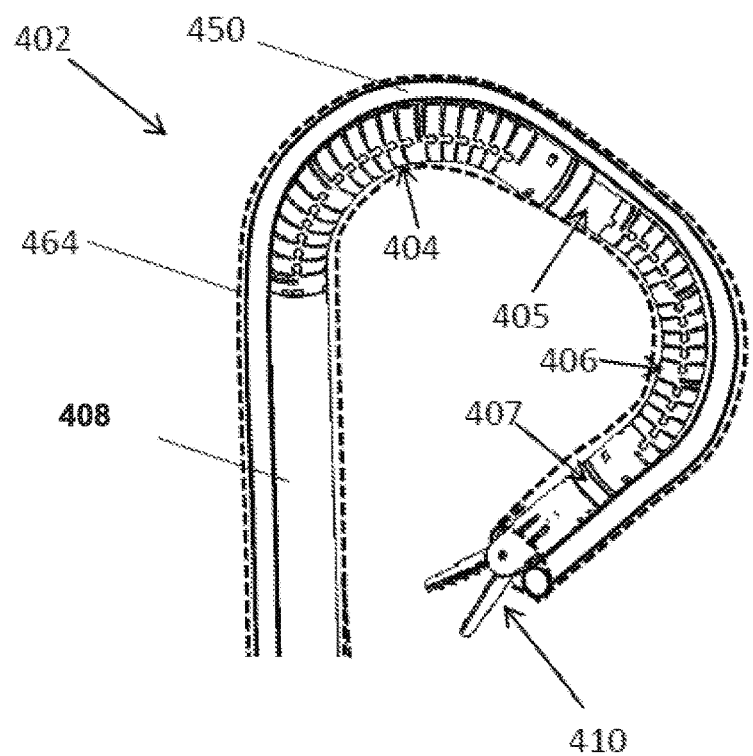
FIG. 4B is a simplified schematic of a surgical mechanical arm including a laser device, according to some embodiments of the invention.
Figure 4C:
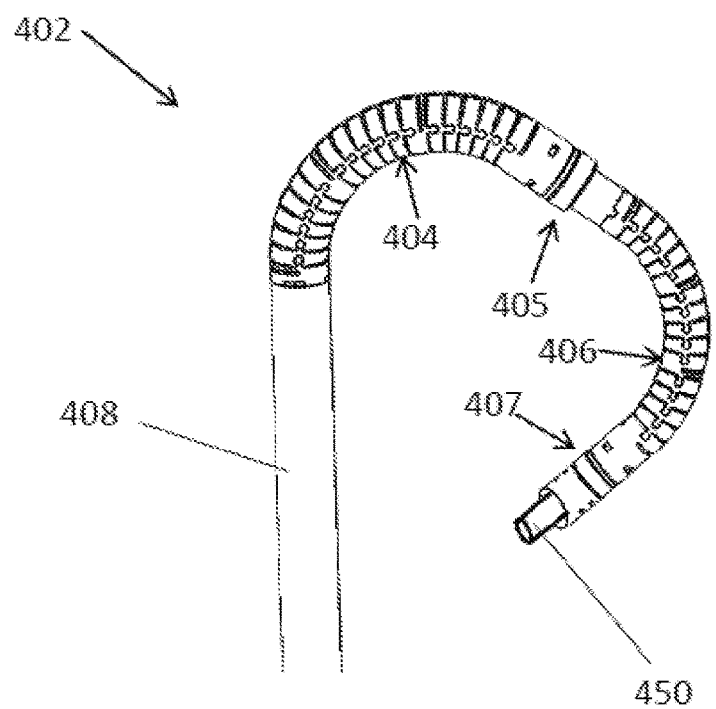
FIG. 4C is a simplified schematic of a surgical mechanical arm including a laser device, according to some embodiments of the invention.

In some embodiments, laser 450 is coupled to the surgical mechanical arm, so that, for example, under forces due to manipulation of the surgical mechanical arm, the laser slides longitudinally within connectors for example, where connectors are not fixed to both the laser and the arm e.g. connectors 456, 457, 458. A potential advantage of the ability of the laser to slide being reduction in one or more force (e.g. tensile force and/or compressive force and/or torque) on laser 450 as the arm is moved into different configurations e.g. by bending at flexible portions 404, 406 and/or rotation of portions about portion long axes. In some embodiments, for example as shown in FIGS. 4A-4C, a rigid portion 405 connects flexible portions 404 and 406, and, in some embodiments, a second rigid portion 407 connects between flexible portion 406 and an end effector 410, such as a gripper. In some embodiments, flexible portion 404 extends from a rigid support portion 408.

FIG. 4B is a simplified schematic of a surgical mechanical arm 402 including a laser 450, according to some embodiments of the invention.

In some embodiments, surgical mechanical arm 402 includes one or more feature as illustrated and/or described regarding surgical mechanical arm 102 FIG. 1.

In some embodiments, for example, as an alternative or addition to connectors (e.g. connector/s as illustrated and/or described regarding FIG. 4A) a sheath 464 couples laser 450 and the surgical mechanical arm, e.g. by surrounding at least an axial portion of both the surgical mechanical arm and laser 450. In some embodiments, sheath 464 is flexible, for example minimally resisting bending at arm flexible portions 406, 404. In some embodiments, sheath 464 includes elastic material. In some embodiments, sheath is electrically insulating and/or includes electrically insulating material. In some embodiments, sheath 464 includes silicone rubber. In some embodiments, an outer surface of the laser and/or inner surface of sheath is low friction, for example, potentially enabling longitudinal movement of the laser within the sheath e.g. longitudinal movement with respect to the arm.

FIG. 4C is a simplified schematic of a surgical mechanical arm including a laser device, according to some embodiments of the invention.

In some embodiments, surgical mechanical arm 402 includes one or more feature as illustrated and/or described regarding surgical mechanical arm 102 FIG. 1.

In some embodiments, laser 450 is coupled to the surgical mechanical arm by being disposed with a hollow channel within the arm. Potentially, locating the laser within the arm reduces bending of the laser as the arm is moved into different positions. A potential advantage being reduced forces on the laser as the arm is manipulated into different configurations. In some embodiments, the laser is held inside the hollow channel within the arm such that it extends along the central axis of the hollow channel. Optionally, centering means such as hooks, clips, spacers, an inner sheath and/or other means are used for maintaining the laser in a central position.

Figure 5:
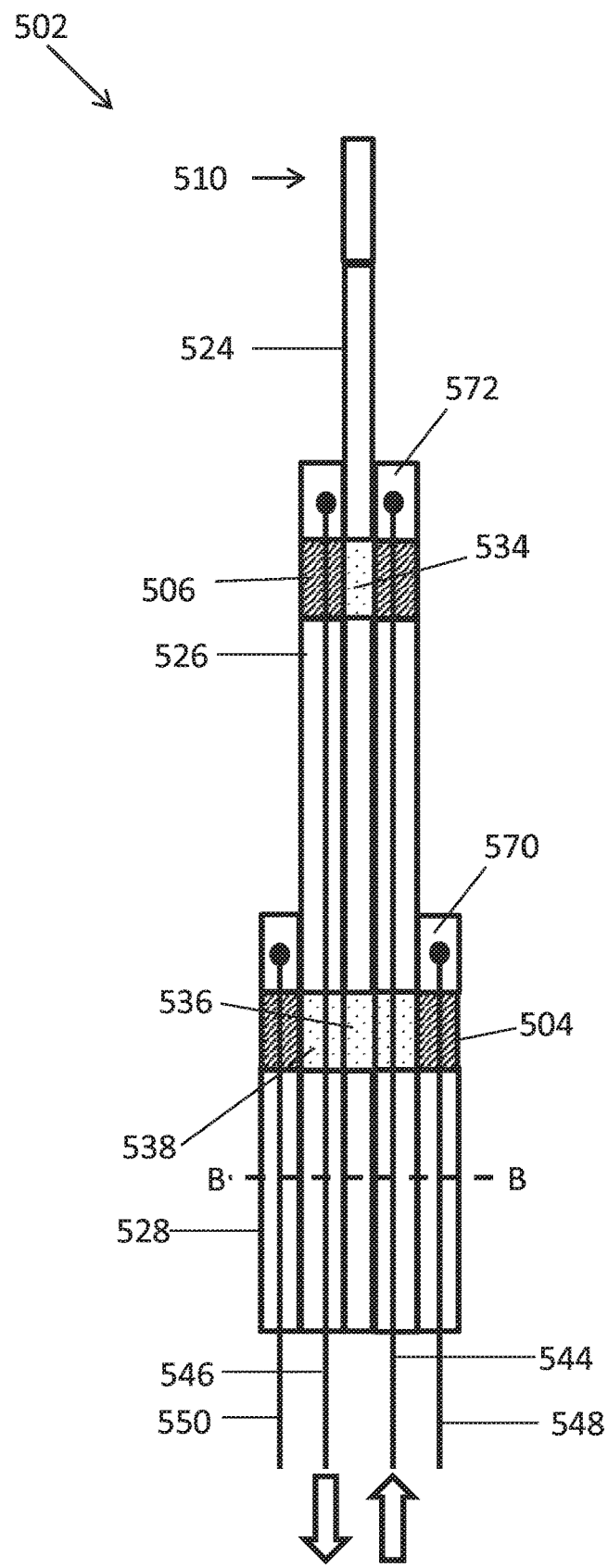
FIG. 5 is a simplified schematic cross section of a mechanical arm, according to some embodiments of the invention.

FIG. 5 is a simplified schematic cross section of a mechanical arm 502, according to some embodiments of the invention.

In some embodiments, mechanical arm 502 includes a first and a second flexible portion 504, 506 respectively. In some embodiments, mechanical arm 502 includes one or more nested tubular structures. In some embodiments, the mechanical arm includes an inner tubular structure 524, an intermediate tubular structure 526 and an outer tubular structure 528.

In some embodiments, one or more tubular structure includes a flexible portion and/or a torque transfer portion. In some embodiments, for example as shown in FIG. 5, dotted fill indicates a torque transfer portion and angled shading indicates a flexible portion, where one or more torque transfer portion includes one or more feature as illustrated and/or described regarding International Patent Application No. WO2016/035084 which is herein incorporated by reference in its entirety.

In some embodiments, inner tubular structure 524 includes a first and a second torque transfer portion 536, 534, respectively.

In some embodiments, intermediate tubular structure 526 includes a torque transfer portion 538 and a first flexible portion 504.

In some embodiments, outer tubular structure 528 includes a flexible portion 504.

In some embodiments, flexion of one or more of flexible portions 504, 506 is controlled by changing tension on one or more element coupled to a portion of the surgical mechanical arm.

In some embodiments, flexion of first flexible portion 504 is controlled by one or both of first flexible portion cables 550, 548. Similarly, in some embodiments, flexion of second flexible portion 506 is controlled by one or both of second flexible portion cables 544, 546.

In some embodiments, one or more flexible portion is controlled by more than two cables, for example, 3-15, or 3-10, or 3-6 cables, or lower or higher or intermediate numbers or ranges of cables. In some embodiments, one or more flexible portion is controlled by a single cable.

In some embodiments, one or more cables runs through a hollow passageways within a solid portion of the mechanical arm. In some embodiments, a cable runs through a hollow passageway within a tubular portion.

In some embodiments, a distal portion of arm 502 e.g. a distal portion of inner tubular structure 524 is rotatable by rotation of a proximal portion of the inner tubular structure.

In some embodiments, one or more (e.g. all) tubular structure is rigid between flexible portions and/or proximally of distal portions.

Figure 6A:
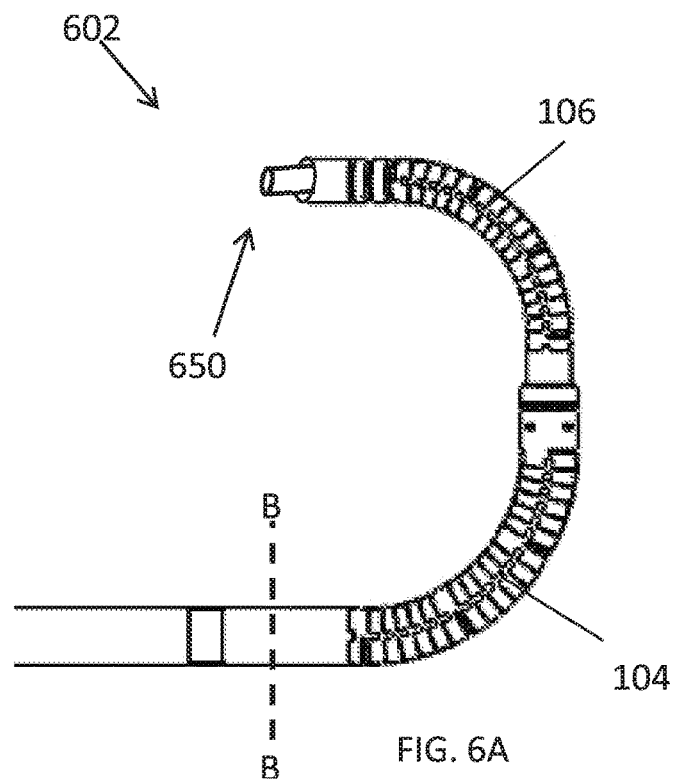
FIG. 6A is a simplified schematic of a distal portion of a surgical mechanical arm including a laser, according to some embodiments of the invention.
Figure 6B:
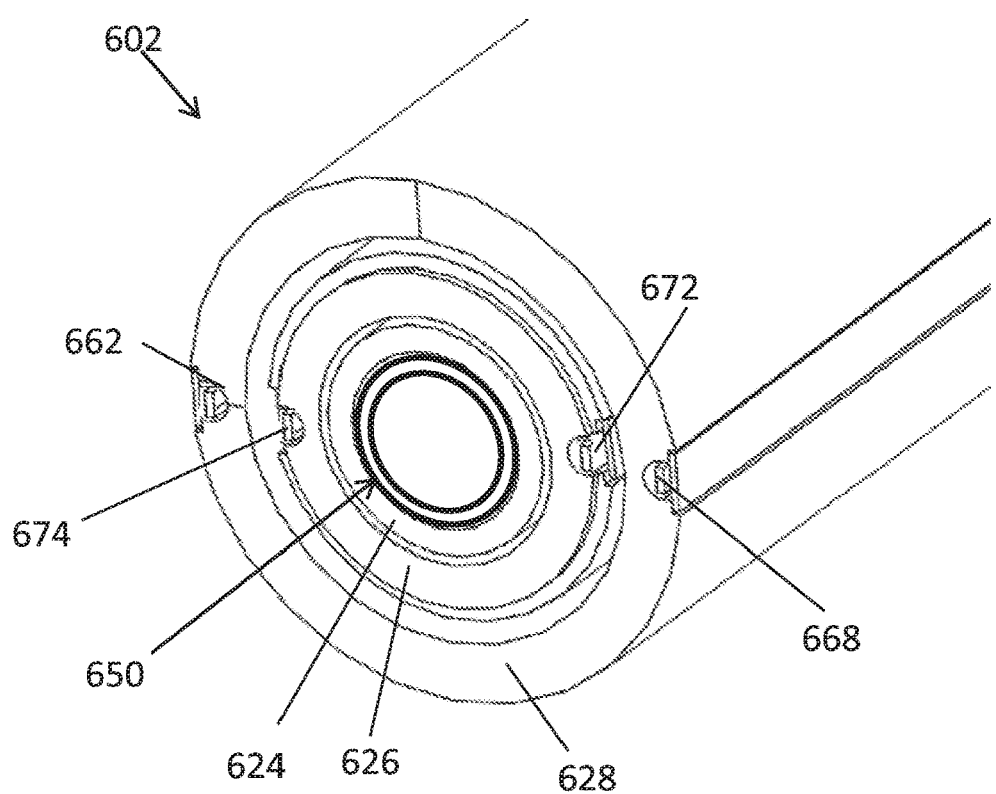
FIG. 6B is a simplified schematic section view of a mechanical arm, according to some embodiments of the invention.

In some embodiments, end effector 510 includes one or more laser tool (e.g. including one or more feature as described regarding and/or illustrated in FIGS. 6A-B and/or 7A-B and/or 8A-B). In some embodiments end effector 510 includes one or more electrosurgical tool (e.g. including one or more feature as described regarding and/or illustrated in FIGS. 7A-B and/or 8A-B). In some embodiments, end effector 510 includes one or more mechanical tool (e.g. including one or more feature as described regarding and/or illustrated in FIGS. 8A-B).

In some embodiments, a mechanical tool, is actuated (e.g. where, in some embodiments, actuation includes opening and/or closing of a gripper and/or scissor tool) by rotation of element/s coupled to the end effector. In some embodiments, actuation of an end effector by rotation includes one or more feature as described and/or illustrated regarding FIGS. 36A-B of International Patent Application No. WO2016/035084 and/or FIGS. 11A-C and 12A-B of U.S. patent application No. 62/583,543, which applications are incorporated by reference in their entireties.

Alternatively or additionally, in some embodiments, end effector 510 is actuated by changing tension on one or more control cable e.g. by "push-pull" where actuation is effected by tensioning one or more control cable while relaxing other control cable/s.

In some embodiments, one or more tubular structure is coupled to another tubular structure (e.g. a tubular structure is coupled to a structure surrounding it). In some embodiments, outer tubular structure 528 is coupled to intermediate tubular structure 526 by connector 570. In some embodiments, intermediate tubular structure 526 is coupled to inner tubular structure 524 by connector 572. In some embodiments, one or more of connectors 570, 572 prevent axial movement of the tubular structures with respect to each other. Additionally or alternatively, in some embodiments, one or more of connectors 570, 572, include bearings which facilitate rotation of tubular structures (e.g. each tubular structure about its long axis and/or about a long axis of the arm) with respect to each other.

FIG. 6A is a simplified schematic of a distal portion of a surgical mechanical arm 602 including a laser tool 650, according to some embodiments of the invention.

In some embodiments, arm 602 includes one or more feature as illustrated and/or described regarding arm 102, FIG. 1 (for example, flexible portions 104, 106).

FIG. 6B is a simplified schematic section view of a mechanical arm 602, according to some embodiments of the invention. In some embodiments, FIG. 6B illustrates a cross section of the surgical mechanical arm of FIG. 6A taken along the dashed line labeled BB.

Visible in FIG. 6B are an outer tubular structure 628, an intermediate tubular structure 626 and an inner tubular structure 624. In some embodiments, one or more of structures 624, 626, 628, include one or more feature as illustrated and/or described regarding structures 524, 526, 528, FIG. 5 respectively.

In some embodiments, a laser cable (e.g. including laser waveguide/s carrying laser light to a laser tool e.g. laser tool 650 FIG. 6A) is disposed within a hollow channel within arm 602, for example, within a hollow passageway of inner tubular structure 624. In some embodiments, for example, where the laser light is generated by a $CO_2$ laser, the waveguide is hollow e.g. tubular e.g. as illustrated by waveguide 650 in FIG. 6B. In some embodiments, an outer diameter of laser tool 650 is smaller than an inner diameter of inner tubular structure 624.

In some embodiments, a waveguide has a circular cross section e.g. is cylindrical. In some embodiments, a waveguide has a square or rectangular cross section.

In some embodiments, a cross sectional diameter of laser tool 650 is selected to be as large as possible while freely moving, in one or more direction within the hollow passageway of inner tubular structure 624. In some embodiments, sizing and/or frictional properties of an external surface of the laser cable and/or inner surface of the inner tubular structure enable relative movement between laser tool 650 and inner tubular structure 624. In some embodiments, movement of laser tool 650 includes longitudinal sliding portion/s of the laser within the hollow e.g. potentially reducing tension and/or compressive forces on laser tool 650 during bending of arm 602. For some embodiments, the inner tubular structure rotates about an inner tubular structure long axis while laser tool 650 remains rotationally static and/or rotates at a different speed and/or direction e.g. potentially reducing torque on the laser cable.

In some embodiments, arm 602 includes one or more control cable 672, 674, 662, 668, where, in some embodiments, control cables include one or more feature as illustrated and/or described regarding control cables 544, 546, 548, 550 FIG. 5 respectively. In some embodiments, one or more control cable is housed in a channel within a wall of a tubular structure. In some embodiments, channel/s are formed by a trench within the tubular structure wall which is, in some embodiments, covered, at least partially with cover/s.

Figure 7A:
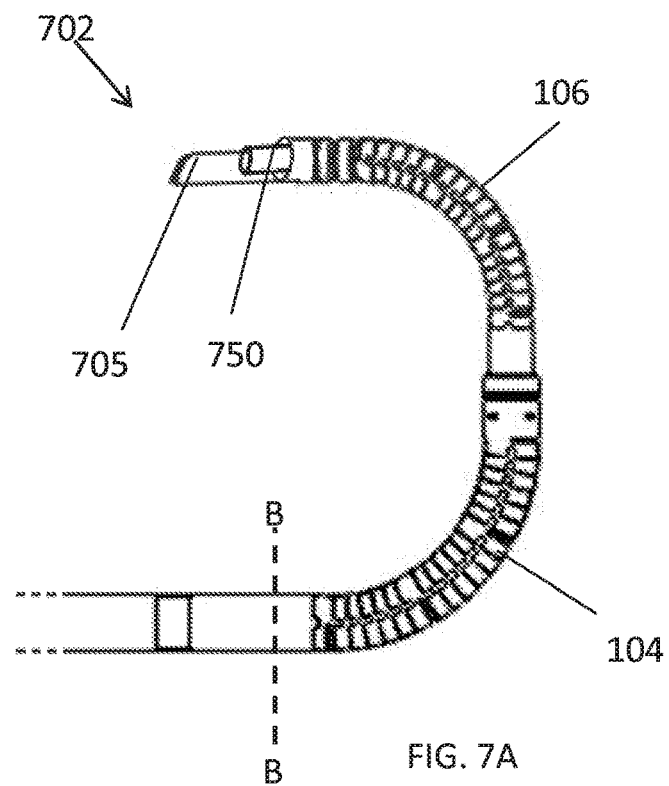
FIG. 7A is a simplified schematic of a distal portion of a surgical mechanical arm including a laser and a monopolar tool, according to some embodiments of the invention.

FIG. 7A is a simplified schematic of a distal portion of a surgical mechanical arm including a laser and a monopolar tool, according to some embodiments of the invention.

In some embodiments, arm 702 includes one or more feature as illustrated and/or described regarding arm 102, FIG. 1 (for example, flexible portions 104, 106).

Figure 7B:
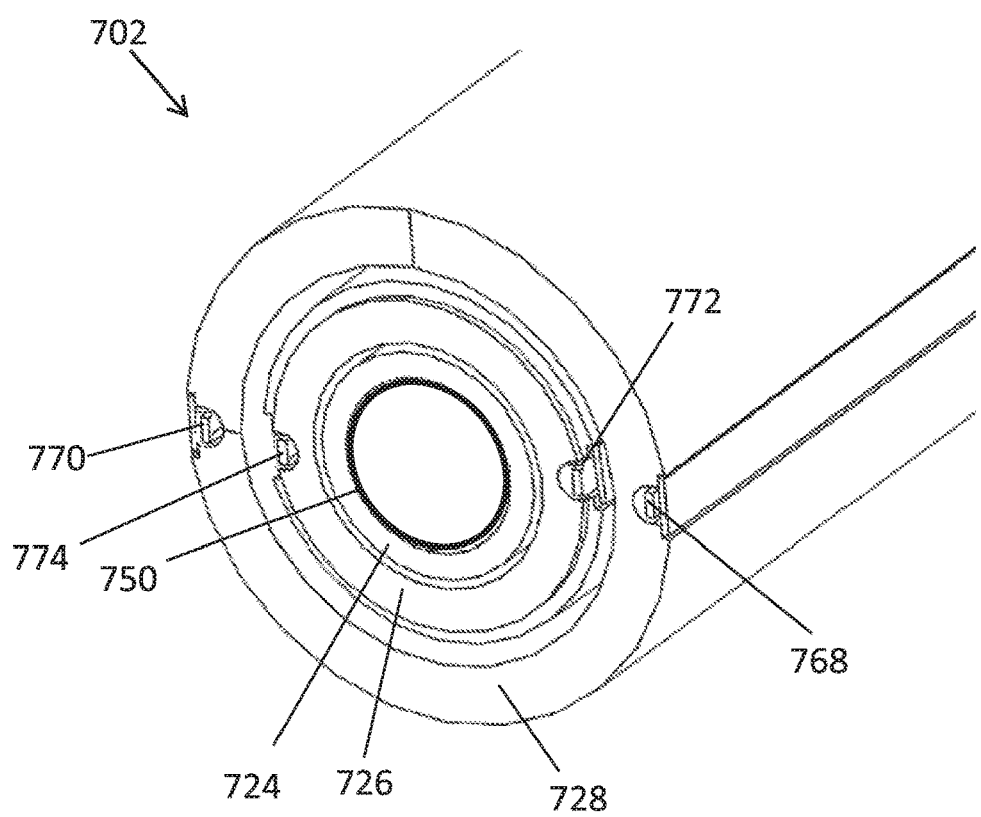
FIG. 7B is a simplified schematic section view of a mechanical arm, according to some embodiments of the invention.

FIG. 7B is a simplified schematic section view of a mechanical arm, according to some embodiments of the invention. In some embodiments, FIG. 7B illustrates a cross section of the surgical mechanical arm of FIG. 7A taken along the dashed line labeled BB.

In some embodiments, a laser cable (e.g. including cable/s carrying laser light to a laser tool e.g. laser tool 750 FIG. 7A) is disposed within a hollow channel within arm 702.

In some embodiments, arm 702 includes an electrosurgical tool 705 (see FIG. 7A). In some embodiments, tool 705 is a monopolar tool (e.g. a monopolar scalpel and/or spatula). In some embodiments, electrosurgical power is supplied to tool 705 though a body of the arm. In some embodiments, arm portions proximal of the electrosurgical tool are covered by an insulating sheath.

In some embodiments, a cross sectional diameter of laser cable 750 is selected to be as large as possible while freely moving, in one or more direction within the hollow passageway of inner tubular structure 724. In some embodiments, sizing and/or frictional properties of an external surface of the laser cable and/or inner surface of the inner tubular structure enable relative movement between laser cable 750 and inner tubular structure 724. In some embodiments, movement of laser cable 750 includes longitudinal sliding portion/s of the laser within the hollow e.g. potentially reducing tension and/or compressive forces on laser cable 750 during bending of arm 702. For some embodiments, the inner tubular structure rotates about an inner tubular structure long axis while laser cable 750 remains rotationally static and/or rotates at a different speed and/or direction e.g. potentially reducing torque on the laser cable.

Visible in FIG. 7B are an outer tubular structure 728, an intermediate tubular structure 726 and an inner tubular structure 724. In some embodiments, one or more of structures 724, 726, 728, include one or more feature as illustrated and/or described regarding structures 524, 526, 528, FIG. 5 respectively.

In some embodiments, arm 702 includes one or more control cable 772, 774, 770, 768, where, in some embodiments, control cables include one or more feature as illustrated and/or described regarding control cables 544, 546, 548, 550 FIG. 5 respectively. In some embodiments, one or more control cable is housed in a channel within a wall of a tubular structure. In some embodiments, channel/s are formed by a trench within the tubular structure wall which is, in some embodiments, covered, at least partially with cover/s.

Figure 8A:
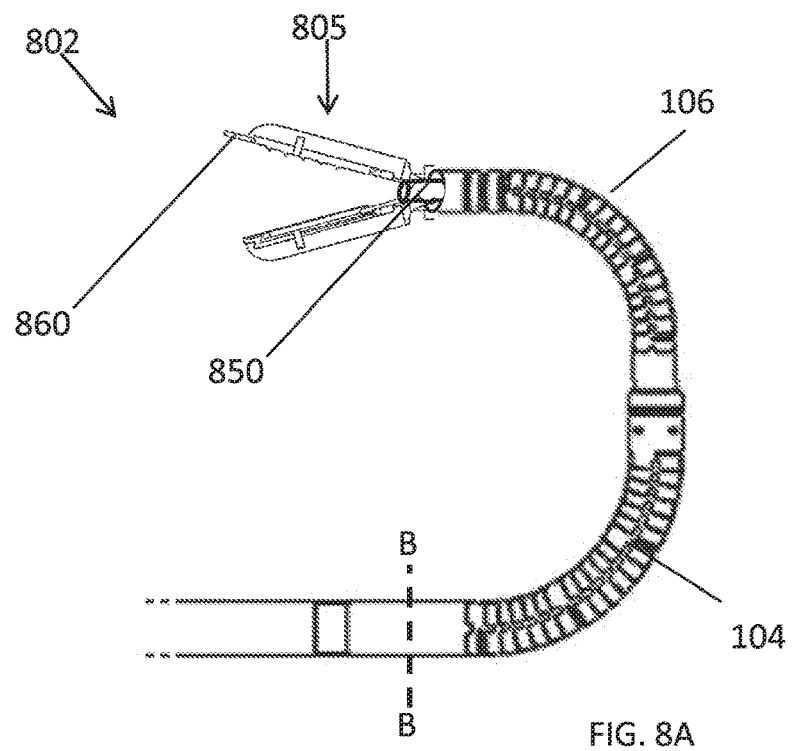
FIG. 8A is a simplified schematic of a distal portion of a surgical mechanical arm including a laser and a gripper, according to some embodiments of the invention.

FIG. 8A is a simplified schematic of a distal portion of a surgical mechanical arm including a laser tool 850 and a gripper tool 805, according to some embodiments of the invention.

In some embodiments, arm 802 includes one or more feature as illustrated and/or described regarding arm 102, FIG. 1, (for example, including flexible portions 104, 106).

Figure 8B:
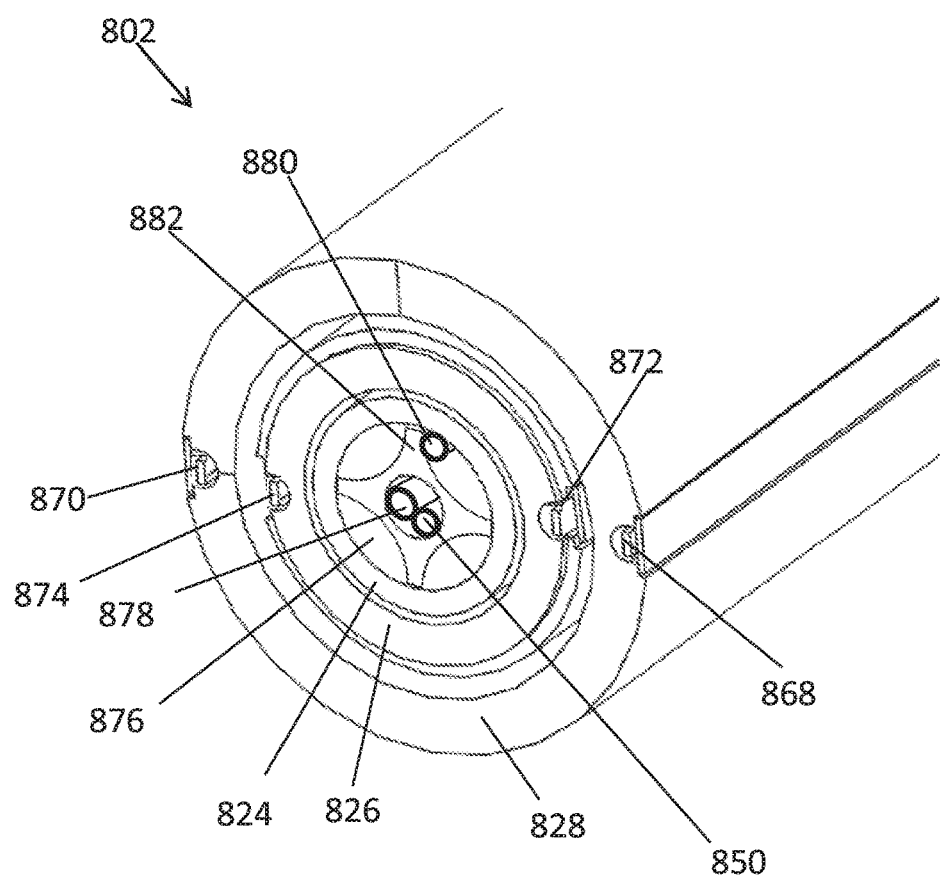
FIG. 8B is a simplified schematic section view of a mechanical arm, according to some embodiments of the invention.

FIG. 8B is a simplified schematic section view of a mechanical arm, according to some embodiments of the invention. In some embodiments, FIG. 8B illustrates a cross section of the surgical mechanical arm of FIG. 8A taken along the dashed line labeled BB.

Visible in FIG. 8B are an outer tubular structure 828, an intermediate tubular structure 826 and an inner tubular structure 824. In some embodiments, one or more of structures 824, 826, 828, include one or more feature as illustrated and/or described regarding structures 524, 526, 528, FIG. 5 respectively.

In some embodiments, a hollow passageway 876 within inner tubular structure 824 houses one or more of: a laser cable (e.g. including laser fiber/s carrying laser light to a laser tool e.g. laser tool 850 FIG. 8B) an end effector control element 878, and an end effector electrosurgical supply cable 880.

In some embodiments, a single type of electrosurgical power supply (e.g. monopolar) is supplied to tool 805 (see FIG. 8A) by cable 880.

In some embodiments, tool 850 is used as a monopolar scalpel. In some embodiments, a monopolar spatula 860 (see FIG. 8A) is placed in close proximity and/or contacted to tissue to perform electrosurgery (e.g. cut) the tissue.

Alternatively or additionally, in some embodiments, a first polarity of electrosurgical power supply is supplied through a body of the arm 802 and a second polarity through cable 880 e.g. for bipolar electrosurgery, where, in some embodiments, tissue grasped between portions of gripper 805 is electrosurgical treated (e.g. coagulated).

In some embodiments, gripper is not charged and is used to grasp tissue e.g. whilst treating the tissue with laser tool 850.

In some embodiments, arm 802 is switchable between two or more of modes; monopolar electrosurgery, bipolar electrosurgery, and lasing. In some embodiments, arm 802 performs lasing and electrosurgery simultaneously.

In some embodiments, control element 878 and/or cable 880 and/or laser cable 850 are supported by a support structure 882, where, in some portion/s of the arm control element 878 is a shaft and in some portion/s of the arm control element 878 is a cable e.g. a torque cable.

In some embodiments, support structure 882 separates cables e.g. reducing friction between the cables. In some embodiments, an additional support structure (not illustrated) separates control element 878 and laser cable 850.

In some embodiments, end effector control element 878 (e.g. including, in some embodiments, a torque cable and/or a shaft) controls actuation of the end effector (e.g. end effector 860 FIG. 8A e.g. opening and/or closing of the two portions of the gripper 860). In some embodiments, end effector control element 878 is configured to transfer torque to the end effector, which actuates the end effector, for example, opening and/or closing a gripper or scissors end effector. In some embodiments, control element 878 transfers torque applied by a motor e.g. located proximally of the end effector and/or at a proximal end of the articulated arm.

Alternatively or additionally, in some embodiments, the end effector is actuated by changing tension on one or more control cable coupled to the end effector (e.g. a by "push pull") e.g. including one or more feature as described and/or illustrated regarding tool actuation in U.S. Pat. No. 9,039,057 which is herein incorporated by reference in its entirety.

In some embodiments, arm 802 includes one or more control cable 872, 874, 870, 868, where, in some embodiments, control cables include one or more feature as illustrated and/or described regarding control cables 544, 546, 548, 550 FIG. 5 respectively. In some embodiments, one or more control cable is housed in a channel within a wall of a tubular structure. In some embodiments, channel/s are formed by a trench within the tubular structure wall which is, in some embodiments, covered, at least partially with cover/s.

Exemplary Method of Control

FIG. 9 is a flow chart of a method of laser tool control, according to some embodiments of the invention.

At 900, in some embodiments, for one or more axial portion of a laser device, a projected curvature and/or torque for the axial portion is estimated. In some embodiments, estimating is performed by a processor (e.g. processor 110 FIG. 1). Optionally, estimating is performed in accordance with a position indication, e.g. a position indication received from one or more sensors in the motor unit (e.g. encoders) and/or one or more sensors in or on the surgical arm segments.

At 902, in some embodiments, one or more control signal is generated and/or changed based on the estimated curvature. In some embodiments, a control signal instructing a laser tool to begin lasing is enabled and/or disabled, based on the estimated curvature and/or torque. In some embodiments, control signals for control of actuator/s to move the surgical mechanical arm/s are changed and/or generated based estimated laser curvature and/or torque.

In some embodiments, based on the estimated curvature, movement of the surgical mechanical arm is limited or prevented. In some embodiments, based on the estimated curvature, an alert is generated (e.g. via the user interface) when reaching a predetermined threshold. In some embodiments, based on the estimated curvature, an alternative path for reaching a similar end position of the surgical mechanical arm and/or laser tool is suggested, for example, by optimizing bending angles and/or orientation of surgical arm portions.

Figures 10A, 10B, 10C:
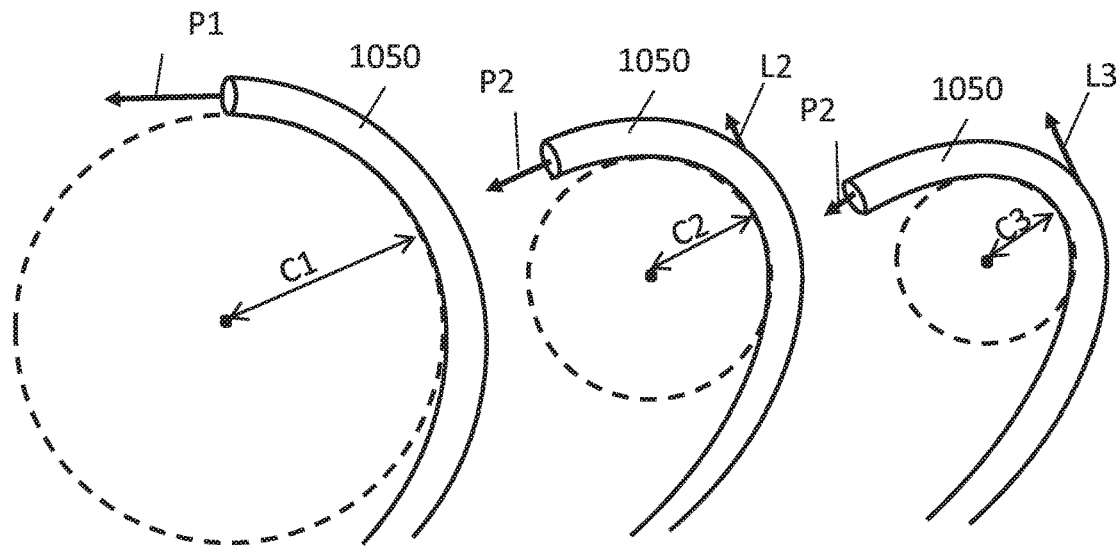
FIGS. 10A-C are simplified schematics of a laser cable with different curvatures, according to some embodiments of the invention.

FIGS. 10A-C are simplified schematics of a laser cable 1050 with different curvatures C1, C2, C3, according to some embodiments of the invention.

In some embodiments, FIG. 10A illustrates a radius of curvature C1, where there is little or no leakage of laser power. In some embodiments, FIG. 10B illustrates a radius of curvature C2, where there is leakage, L2 of laser power. In some embodiments, FIG. 10C illustrates a radius of curvature C3, where there leakage, L3 of laser power.

In some embodiments, decreasing radii of curvature C1>C2>C3 are associated with increasing of leakage of laser power where emitted laser powers P1, P2, P3 decrease with radii of curvature and leakage of laser power increases; L2<L3.

In some embodiments, leakage of laser power from the laser cable occurs under a threshold radius of curvature e.g. where the threshold is C2. In some embodiments, damage occurs to the laser cable under a threshold radius of curvature e.g. where the threshold is C3. In some embodiments, thresholds C2 and C3 increase with torque applied to the laser cable and/or with duration of time that the laser is held within a range of curvatures.

Figures 11A, 11B:
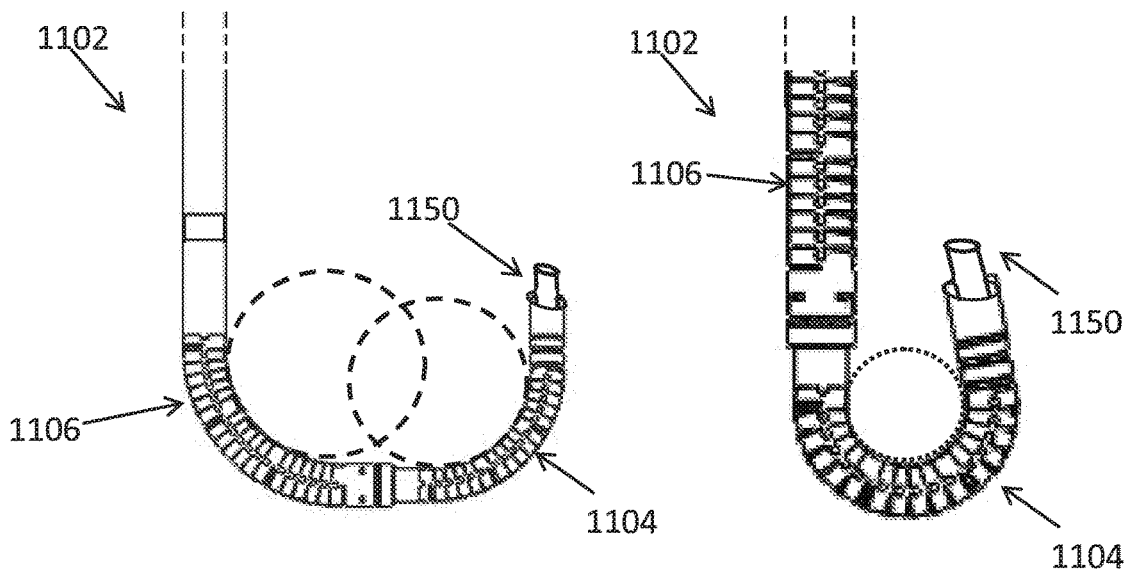
FIGS. 11A-B are simplified schematics of a surgical mechanical arm 1102 including a laser tool 1150 and flexible portions 1104, 1106, according to some embodiments of the invention.

FIGS. 11A-B are simplified schematics of a surgical mechanical arm 1102 including a laser tool 1150 and flexible portions 1104, 1106, according to some embodiments of the invention.

In some embodiments, sensing and/or estimation of curvature is a plurality of different axial portions of the surgical mechanical arm, for example, for each of flexible portions 1104, 1106 of the surgical mechanical arm. In some embodiments, a control signal for each flexible portion is generated and/or adjusted based on curvature and/or projected curvature of the portion.

Exemplary Methods of Treatment

FIG. 12 is a flow chart of a method of laser treatment, according to some embodiments of the invention.

At 1200, in some embodiments, data regarding laser curvature and/or from which laser curvature and/or projected laser curvature based on user input/s is received.

In some embodiments, data includes measurement/s of current laser curvature, for example, as provided by one or more sensor e.g. sensor/s 194 FIG. 1. In some embodiments, data includes curvature and/or torque of portion/s of arm (e.g. data from strain gauge e.g. contact sensor).

In some embodiments, data includes image/s e.g. collected by one or more camera and/or imaging device. In some embodiments, an optical camera is inserted with the surgical mechanical arm/s which captures image/s of the arm/s, for example, sensor/s of an imaging device e.g. x-ray, ultrasound, CT, MRI.

In some embodiments, data includes user control inputs, for example: arm actuator control signal/s (e.g. stored in a memory), data from input device sensor/s (e.g. sensor/s 108) and/or sensor/s measuring a posture of one or more input device (e.g. input device 106 FIG. 1). Alternatively or additionally, in some embodiments, data includes user inputs through user interfaces (e.g. one or more of user interfaces 240, 236, 234 FIG. 2). In some embodiments, user inputs include one or more of: a user input to lase using a laser tool, a user input to control laser parameters.

In some embodiments, data is received for a plurality of different axial portions of the surgical mechanical arm, for example, for each flexible portion of the surgical mechanical arm (e.g. flexible portions 104, 106 FIG. 1).

In some embodiments, data is received regarding torque forces on one or more portion of the laser.

Optionally, in some embodiments, received data is saved, for example, with respect to time.

At 1202, in some embodiments, current and/or projected curvature of laser cable/s is estimated e.g. using data received in step 1200. In some embodiments, curvatures are estimated for different axial portions of the laser e.g. the portion bent by flexible portions of the arm.

In some embodiments, bending of arm flexible portions is estimated from data regarding actuator control signal/s.

At 1204, in some embodiments, optionally, for a plurality of axial portions, estimated laser curvature is compared with one or more threshold.

In some embodiments, a leakage threshold radius of curvature is associated with laser leakage when the laser is lasing. In some embodiments, the leakage threshold depends on one or more laser parameter (e.g. power, frequency).

In some embodiments, a damage threshold radius of curvature is associated with laser cable breakage. In some embodiments, the damage threshold radius is independent of whether the laser is lasing or not. In some embodiments, the leakage threshold radius is larger than the breakage threshold radius (the laser cable/s being damaged at smaller radii than radii at which the laser cable/s leak).

In some embodiments, torque data is compared with one or more threshold.

Optionally, at 1206, in some embodiments, laser curvature (and/or laser torque), for one or more portion of one or more laser tool is compared to a duration threshold. In some embodiments, leakage and/or breakage radius of curvature thresholds (and/or torque threshold/s) are time dependent, and, in some embodiments, increase with time at which the laser is held at the radius.

At 1208, in some embodiments, one or more control signal for control of movement of one or more surgical mechanical arm is adjusted and/or generated, for example, for control of a surgical mechanical arm including a laser tool. In some embodiments, a processor generating arm movement control signal/s (e.g. processor FIG. 1) and sending them to arm actuator/s (e.g. motor unit FIG. 1) generates control signals based on received user inputs (e.g. input arm measurement/s) and laser curvature estimate/s (e.g. as described in step 1202) and/or torque estimate/s. In some embodiments, the arm control signal/s are generated based on received user inputs and then adjusted based on laser curvature estimate/s (and/or torque estimate/s).

Alternatively or additionally to step 1208, at 1210, in some embodiments, if the estimated laser curvature (and/or estimated torque) is above and/or within a range of a threshold, an alert is issued to the user, e.g. through one or more user interface. The alert, for example, instructs the user to cease lasing and/or change posture. In some embodiments, different alerts are issued depending on, for example, which of a plurality of thresholds has been breached.

Alternatively or additionally to steps 1208 and/or 1210, at 1212, in some embodiments, if estimated laser curvature (and/or estimated torque) breaches one or more threshold, lasing from laser tool/s and/or movement of surgical mechanical arm/s is disabled.

In an exemplary embodiment, once estimated laser curvature for one or more portion of the laser is above a leakage threshold, lasing is automatically disabled while manipulation of the surgical mechanical arm/s remains enabled.

In an exemplary embodiment, the system allows a user to direct the laser arm into a posture over which leakage occurs, before lasing has been initiated. In some embodiments, once the user enables lasing, the system prevents lasing and/or alerts the user to a level of leakage associated with the current arm posture. In some embodiments, different levels of leakage (e.g. high, medium, low) are indicated. In some embodiments, the system displays to the user alternative postures for the arm (e.g. as described below regarding step 1214), optionally with the alternative posture estimated laser leakage.

Alternatively or additionally to steps 1208, and/or 1210, and/or 1212, at 1214, in some embodiments, an arm posture alternative is generated. In some embodiments, the arm posture alternative is an alternative posture of the arm including linear movement of the arm and/or changing of bending and/or rotation at arm flexible portions to direct the laser towards the same target, but with a lower curvature of one or more of the flexible portions. In some embodiments, software (e.g. hosted by a processor e.g. processor 110 FIG. 1) extracts from sensor data and/or actuator control signal data, a position of the laser tool e.g. with respect to the motor unit. The software generating one or more posture alternative based on known degrees of freedom and/or freedom of movement of the surgical mechanical arm. In some embodiments, posture alternative/s are generated using anatomical maps, e.g. so that movement of the arm into the posture and/or the posture itself does not damage tissue. In some embodiments, the arm is automatically positioning into a posture alternative. In some embodiments, posture alternative/s are displayed to a user, optionally with, for example, estimated associated laser efficiency.

Figure 13:
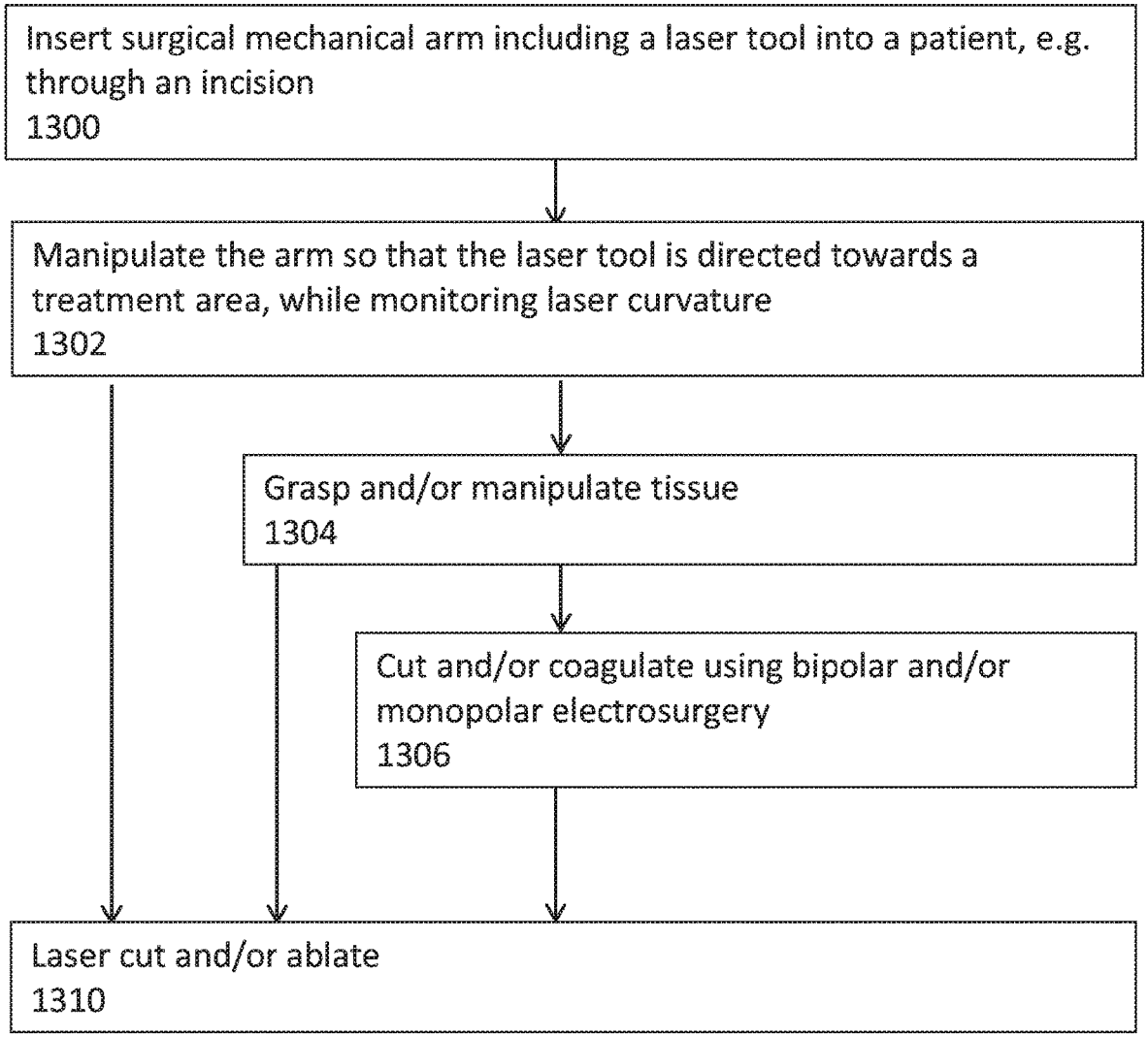
FIG. 13 is a method of treatment, according to some embodiments of the invention.

FIG. 13 is a method of treatment, according to some embodiments of the invention.

At 1300, in some embodiments, a surgical mechanical arm including a laser tool (for example arm 402 FIG. 4A, arm 402 FIG. 4B, arm 402 FIG. 4C, arm 602 FIG. 6A, arm 702 FIG. 7A, arm 802 FIG. 8A) is inserted into a patient. In some embodiments, one or more additional surgical mechanical arm including a laser tool is inserted into the patient. In some embodiments, the arm is inserted into the patient through an incision. In some embodiments, the arm is inserted into a natural orifice. In some embodiments, the arm is inserted into a natural orifice and into the patient through an incision in the orifice.

In some embodiments, the natural orifice is the vagina. In some embodiments, the arm is inserted into the vagina and through an incision in the vagina posterior fornix into the Pouch of Douglas. In some embodiments, the arm is inserted into the vagina and through an incision in the vagina anterior fornix into the abdomen.

In some embodiments, more than one surgical mechanical arm is inserted into the patient. In some embodiments, additional arm/s include laser tool/s and/or electrosurgical tool/s and/or tissue manipulation tool/s.

In some embodiments, the one or more surgical arm is not inserted into the patient and/or are inserted into an orifice but not inserted into an incision but are used at a surface of the patient e.g. in traditional open surgery e.g. to treat skin surface/s.

At 1302, in some embodiments, the surgical mechanical arm including a laser tool is manipulated e.g. so that the laser tool is positioned to treat an area of tissue. In some embodiments, during manipulation, curvature of one or more axial portion of the mechanical arm is monitored and/or controlled (including one or more feature as described and/or illustrated in FIG. 9 and/or FIG. 12).

At 1310, in some embodiments, laser tool/s are activated to treat target tissue, for example, where the laser tool/s cut and/or ablate tissue.

Optionally, in some embodiments, tissue is grasped and/or manipulated (1304), for example, isolated (e.g. moved and/or held away from other tissue) prior to manipulating the arm to a position in which the laser tool is directed towards the treatment area (see 1302).

Figure 15:
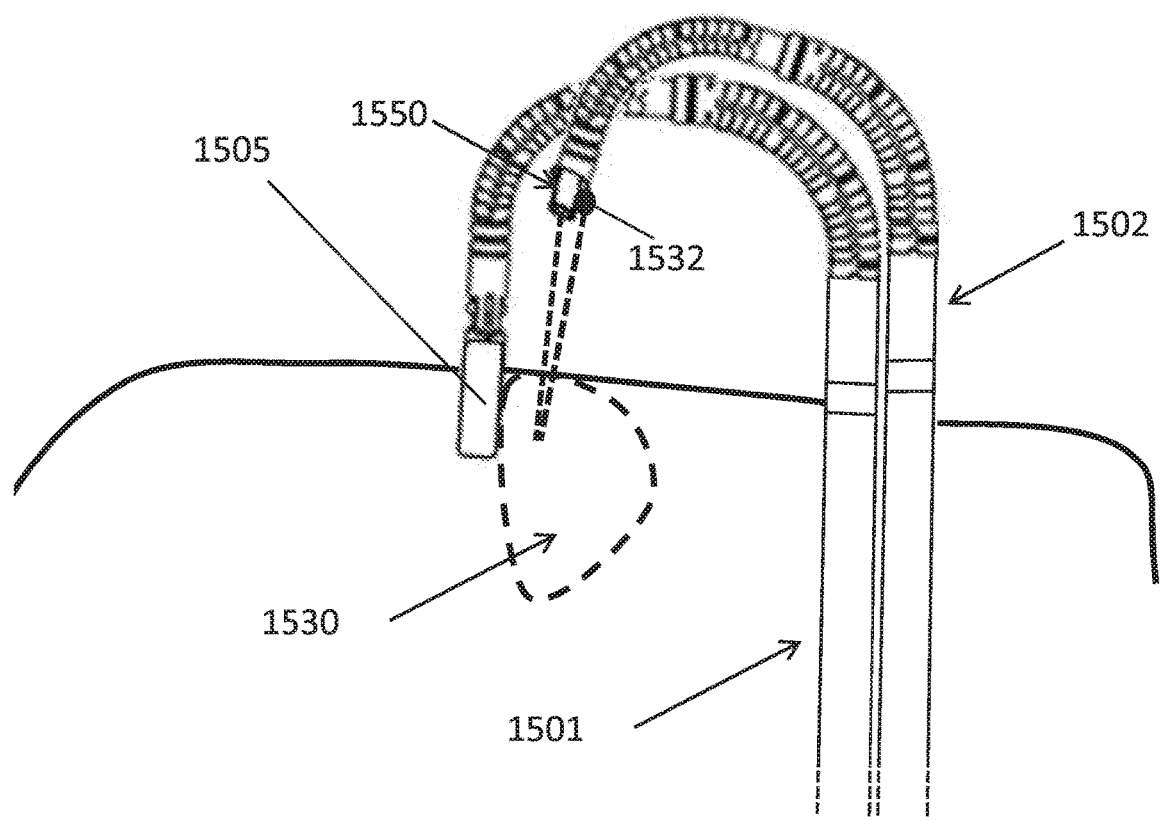
FIG. 15 is a simplified schematic showing treatment of a target with a surgical laser mechanical arm and a surgical mechanical arm, according to some embodiments, of the invention.

In some embodiments, tissue manipulation is performed manually (e.g. in the case of open surgery). In some embodiments, tissue manipulation is performed using traditional laparoscopic tool/s. In some embodiments, tissue manipulation is performed using one or more surgical mechanical arm (e.g. a surgical mechanical arm lacking a laser tool e.g. including one or more feature as described and/or illustrated in U.S. patent application Ser. No. 15/402,342 which is herein incorporated by reference in its entirety), for example, as illustrated in FIG. 15 where arm 1501 grasps tissue and arm 1502 laser treats the tissue.

In some embodiments, tissue manipulation is performed, using a grasping tool which is part of the surgical mechanical arm including the laser tool (e.g. arm 402 FIG. 4A, arm 802 FIG. 8A).

Optionally, at 1306, in some embodiments, tissue is isolated (e.g. separated from other tissue) and/or cut and/or coagulated by electrosurgery.

In some embodiments, electrosurgery is performed using the tool grasping and/or manipulating tissue e.g. as described regarding step 1304.

In some embodiments, tissue manipulation is performed using a grasping and/or cutting tool using bipolar and/or monopolar electrosurgery. In some embodiments, tissue manipulation is performed using one or more surgical mechanical arm e.g. a surgical mechanical arm lacking a laser tool e.g. including one or more feature as described and/or illustrated in U.S. patent application Ser. No. 15/402, 342. In some embodiments, tissue manipulation is performed, for example, using one or more surgical mechanical arm including a laser and a grasping and/or manipulating tool e.g. arm 402 FIGS. 4A-C, arm 702 FIG. 7A, arm 802 FIG. 8A. In some embodiments, electrosurgery is performed before and/or after lasing.

Alternatively or additionally, in some embodiments, electrosurgery is performed by a tool that is not grasping and/or manipulating tissue e.g. by a monopolar tip which, in some embodiments, cuts tissue by contacting tissue without applying force and/or moving the tissue.

At 1310, in some embodiments, the laser tool of the surgical mechanical arm is used to cut and/or coagulate target tissue. In some embodiments, one or more laser tool is used, for example, a laser tool of a second surgical mechanical arm including a laser tool.

In some embodiments, one or more step and/or series of steps are performed repetitively, e.g. as illustrated in FIG. 13. In some embodiments, step 1310 precedes step 1306.

In an exemplary embodiment, the laser tool is used in treatment of endometriosis where the laser tool is used to coagulate by laser ablation "black spots" of endometrium growing external to the inside of the uterus.

In an exemplary embodiment, the laser tool is used in a treatment including removal of an organ or a portion of an organ, for example, hysterectomy, where, in some embodiments, lasing is used to separate the uterus from surrounding tissue.

In an exemplary embodiment, the laser tool is used in treatment of uterine fibroids. In some embodiments, the uterine wall is opened using laser cutting and the fibroid is separated from surrounding tissue by laser cutting. In some embodiments, the fibroid and/or surrounding tissue is grasped and/or manipulated e.g. using one or more feature as described regarding step 1304. In some embodiments, a portion of cutting and/or coagulation is performed by electrosurgery e.g. including one more feature as described regarding step 1306 where, in some embodiments, electrosurgery is performed before and/or after lasing.

In some embodiments, the method is used in treatment of other portions of the body, for example, where insertion of the surgical mechanical arm including a laser tool is into a natural orifice e.g. mouth (e.g. to remove a lesion at the base of the tongue), ear, esophagus, trachea, anus and/or into a portion of the body through an incision e.g. into the lung via an incision in the trachea, e.g. into the abdomen through an incision in the abdominal wall.

FIGS. 14A-D are simplified schematics of a method of treatment using a surgical mechanical laser arm 1402, according to some embodiments of the invention.

Figure 14A:
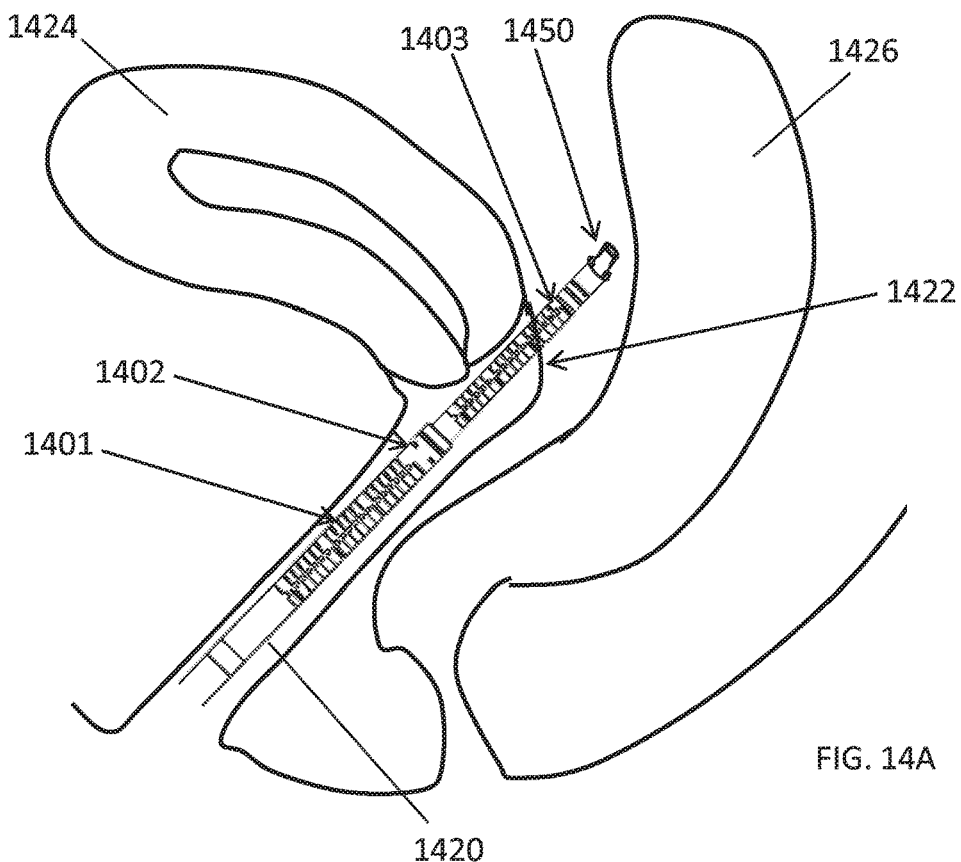
FIGS. 14A-D are simplified schematics of a method of treatment using a surgical mechanical laser arm, according to some embodiments of the invention.

FIG. 14A illustrates a surgical mechanical arm after insertion into a patient's vagina 1420 and through an incision in the vagina (e.g. in posterior fornix 1422) into the abdominal cavity. FIG. 14A illustrates a distal portion of arm 1402 including a laser tool 1450 within the abdominal cavity while a proximal portion of arm 1402 remains within vagina 1420.

Figure 14B:
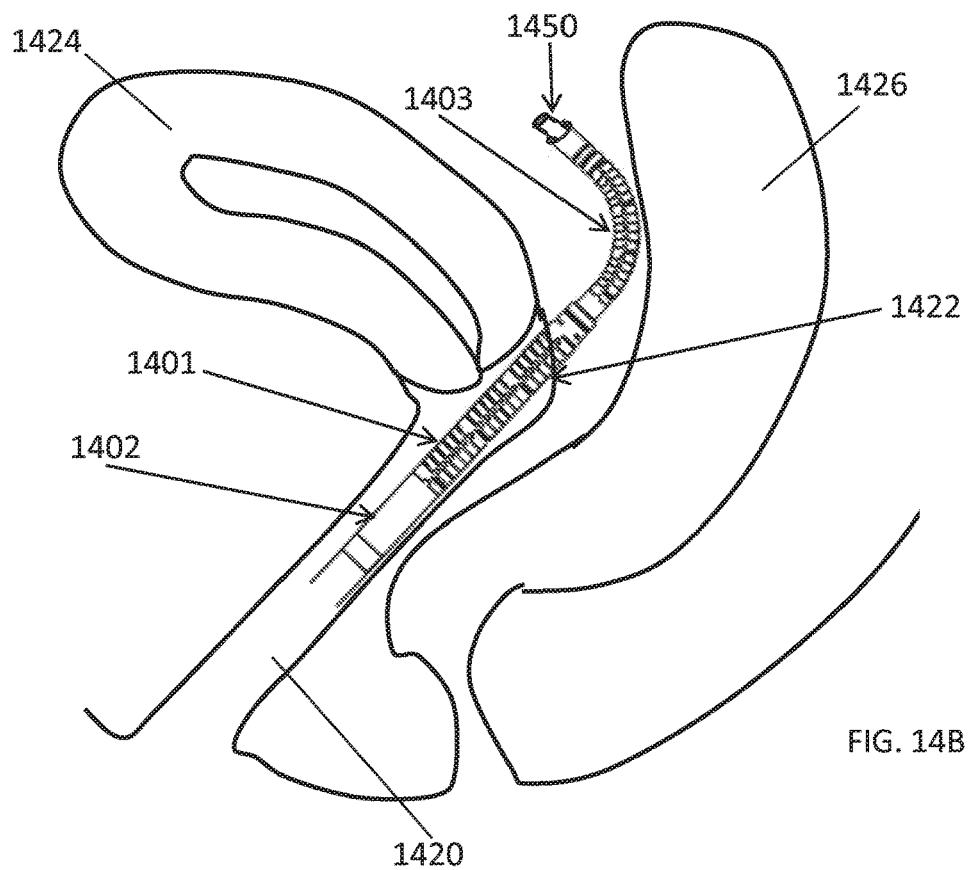

In FIG. 14B arm 1402 has been inserted deeper into vagina 1420 while a second flexible portions 1403 bends e.g. to avoid impinging on the patient's bowel 1426.

Figure 14C:
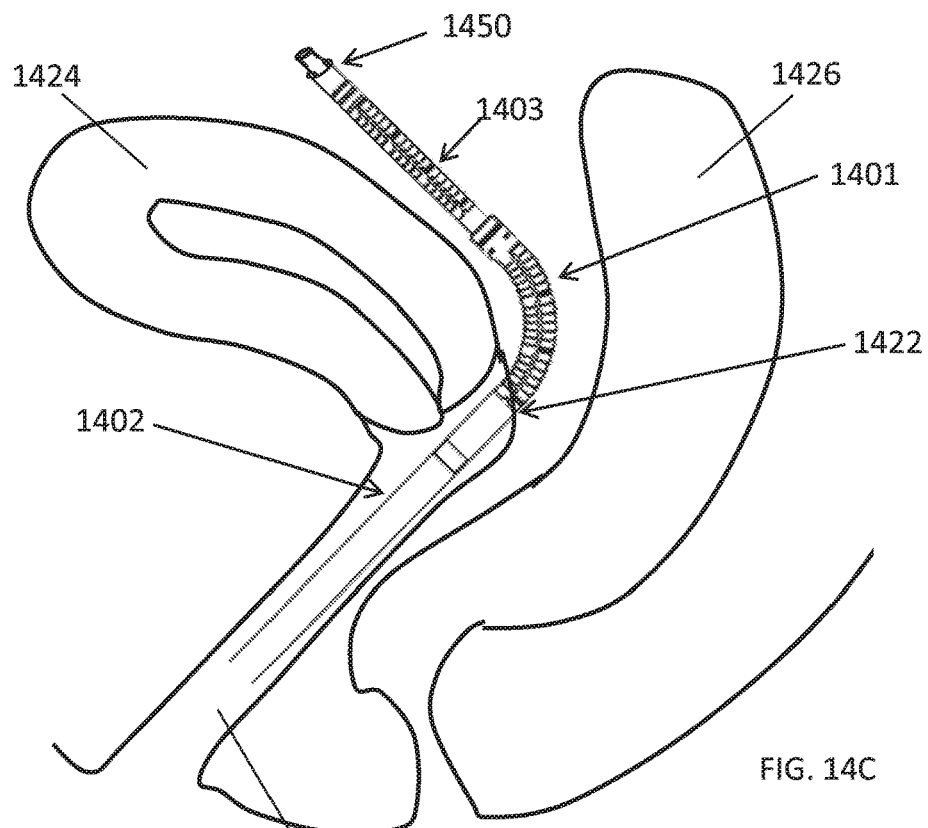

In FIG. 14C arm 1402 has been inserted yet deeper into vagina 1420 while a first flexible portion 1401 has been bent (e.g. to avoid impinging on bowel 1420) and second flexible portion 1403 has been straightened (e.g. to avoid arm 1402 impinging on the patient's uterus 1424).

Figure 14D:
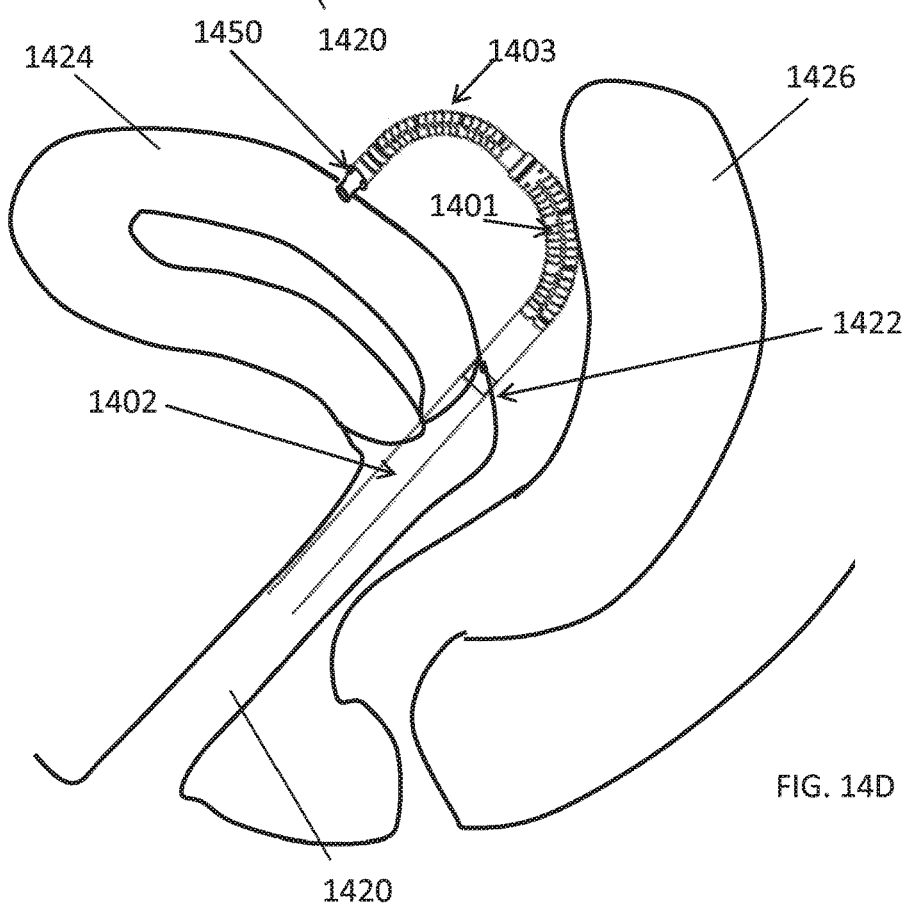

In FIG. 14D arm 1402 has been inserted deeper still into vagina 1420 while bending second flexible portion 1403, for example, to direct laser tool 1450 so that laser light emitted from laser tool 1450 is directed to a treatment site located on uterus 1424.

In some embodiments, movement of the surgical mechanical arm includes retroflection of the arm, for example, to treat a treatment area from a different direction to a direction of insertion and/or entry of the arm into the patient. In some embodiments, as illustrated in FIG. 14D, to treat a portion of a patient (e.g. uterus 1424) from a posterior direction when the arm has been inserted in an inferior direction (e.g. through the uterus). In some embodiments treatment includes one or more feature as illustrated and/or described in International Patent Application Publication No. WO2016035085.

It is noted that systems and/or methods for example as described herein are not limited to procedures performed via the vagina, and other procedures (e.g. involving other natural and/or artificial body entry locations, such as mouth, anus, abdominal port and/or other) are contemplated as well.

FIG. 15 is a simplified schematic showing treatment of a target 1530 with a surgical laser mechanical arm 1502 and a surgical mechanical arm 1501, according to some embodiments, of the invention.

In some embodiments, surgical mechanical arm 1501 includes a tool 1505. In some embodiments, tool 1505 is used to manipulate and/or hold tissue. In some embodiments, tool 1505 is a gripper which, for example, is used, for example, to grip tissue. Alternatively or additionally, in some embodiments, tool 1505 is an electrosurgical tool which is used to cut and/or coagulate tissue (e.g. using monopolar and/or bipolar electrosurgery).

In some embodiments, arm 1502 includes a guiding element 1532, which indicates a region where lasing will occur. Potentially assisting a user in accurate lasing of desired tissue, for example, where lasing is not with visible light (e.g. $CO_2$ lasing). In some embodiments, guiding element 1532 is mounted and/or attached to arm 1502.

In some embodiments, guiding element 1532 is a visible light source, for example a light (e.g. LED, e.g. visible laser) which assists a user directly (e.g. in the case of open surgery) and/or assists a user through collected images (e.g. camera collected images), for example, in laparoscopic treatments.

In some embodiments, guiding element 1532 is a visible light source, which is e.g. attached to arm 1502 such that light emitted from the guiding element, e.g. within a range of separations from the laser tool is directed at a region where the laser will lase e.g. as illustrated by dashed lines in FIG. 15.

In some embodiments, the light source is provided with electrical power by one or more power supply cable, for example, when a light guiding element 1532 is an LED (or other electrically powered light source). In some embodiments, the power supply cable extends from a power supply at the motor unit (e.g. motor unit 114 FIG. 1 e.g. motor unit 218 FIG. 2) through the arm (e.g. through hollow passageways in the arm and/or between the arm and an arm protective sheath) to the light source, e.g. LED.

In some embodiments, the light source is provided by laser light (e.g. visible laser light), where a light waveguide extends through the arm (e.g. through hollow passageways in the arm and/or between the arm and an arm protective sheath). In some embodiments, visible laser light is supplied to the light source by the same laser supply as supplies the laser tool. In some embodiments, visible laser light is supplied to the light source by a different laser supply to that of the laser tool.

Figure 16:
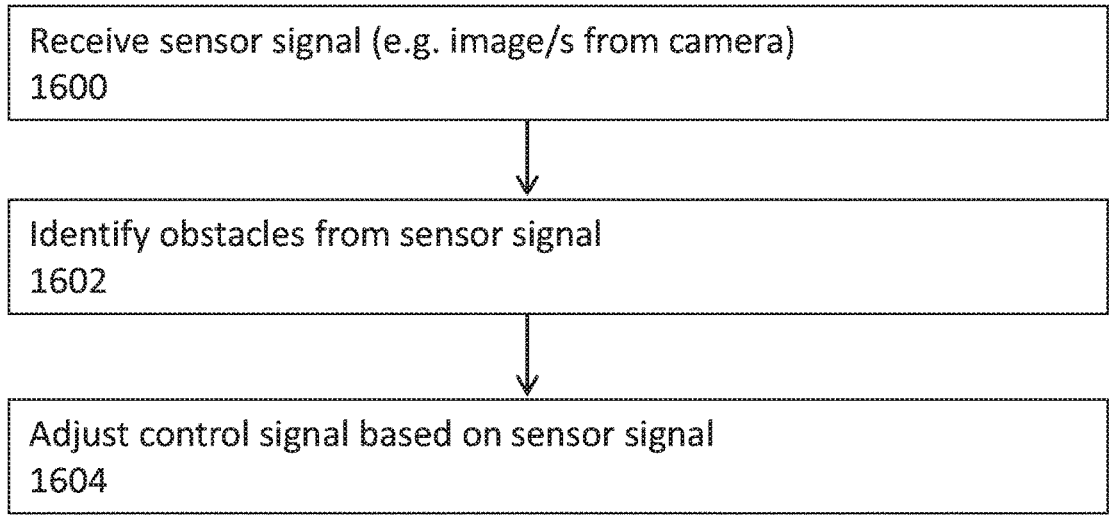
FIG. 16 is a method of laser tool manipulation, according to some embodiments of the invention.

FIG. 16 is a method of laser tool manipulation, according to some embodiments of the invention.

At 1600, in some embodiments, one or more signal from one or more sensor is received (e.g. by a processor e.g. processor 110 FIG. 1). Optionally, the one or more sensor include one or more encoders, optionally located at the motor unit and configured to sense a surgical arm.

In some embodiments, sensor signals include image/s (e.g. optical and/or other modalities e.g. ultrasound, x-ray, CT, MRI). In some embodiments, image/s include images of a treatment space and/or of laser device (e.g. a surgical mechanical arm including a laser tool).

In some embodiments, sensor signals include measurement data from sensor/s measuring laser tool position, for example, input device sensor/s, and/or proximity sensor/s mounted on the laser device.

At 1602, in some embodiments, obstacles are identified from sensor signals received in step 1600. In some embodiments, obstacles are identified from sensor signals e.g. a distance between a laser tool and tissue (e.g. tissue to be treated).

At 1604, in some embodiments, one or more control signal for the laser is adjusted and/or generated based on the sensor signals. In some embodiments, control signal/s for positioning of the laser tool are adjusted and/or generated to prevent the laser tool (e.g. the lasing tip) from contacting tissue directly (e.g. preventing dirt accumulation on the lasing surface, potentially improving laser efficiency). In some embodiments, a separation of the laser tool from a surface to be treated is controlled to maximize laser performance. In some embodiments, the laser tool is maintained at a separation to tissue under a threshold separation where efficiency of laser cutting and/or ablation tissue is reduced (e.g. reduced below a threshold).

Figure 17:
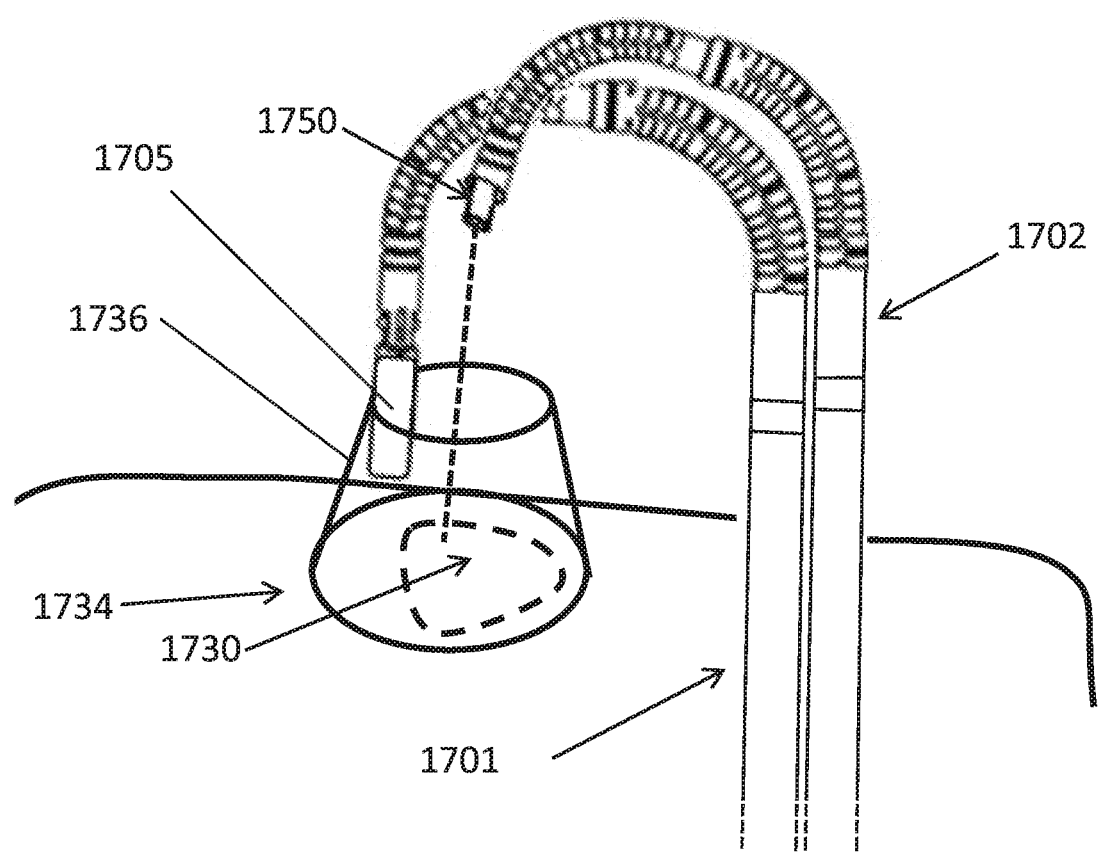
FIG. 17 is a simplified schematic of showing treatment of a target with a surgical laser mechanical arm and a surgical mechanical arm holding a tissue guard, according to some embodiments, of the invention.

FIG. 17 is a simplified schematic showing treatment of a target 1730 with a surgical laser mechanical arm 1702 and a surgical mechanical arm 1701 holding a guard 1736, according to some embodiments, of the invention.

In some embodiments, object/s (e.g. tissue) outside an area of tissue to be laser treated is protected e.g. from receiving laser light from a laser tool 1750 of the surgical laser mechanical arm 1702.

In some embodiments, surgical mechanical arm 1701 positions and/or holds guard 1736 in position where, in some embodiments, guard 1736 absorbs lasing from laser tool 1750.

In FIG. 17, guard 1736 comprises a truncated cone shape, where in some embodiments, arm 1701 positions guard 1736 around a target 1730 tissue treatment area and then laser arm 1702 is positioned within the guard.

In some embodiments, guard/s have different shapes e.g. planar and/or including a planar portion, which may be used as a "cutting board" for example, where the guard and laser tool are positioned between tissue to be cut, the guard preventing deeper tissue from being lazed.

In some embodiments, an arm holds and/or positions more than one guard e.g. one or more guard being fixed in position (e.g. and not held by the arm) during a treatment. In some embodiments, more than one arm positions and/or holds one or more guard. In some embodiments, a surgical mechanical arm itself acts as a guard.

In some embodiments, positioning of guards is using software guidance. In some embodiments, anatomical mapping and/or mapping of positon of the laser arm 1702 and/or of arm 1701 is used to accurately direct lasing and/or other treatment with one or more arm to a treatment site. In some embodiments, anatomical mapping and/or arm position mapping is used to guide positioning of one or more guard. In some embodiments, anatomical mapping and/or arm position mapping is displayed to a user e.g. assisting the user to identify what non-target tissue may be at risk from lazing.

General

It is expected that during the life of a patent maturing from this application many relevant laser technologies will be developed and the scope of the terms laser device, laser tool, laser surgical tool are intended to include all such new technologies a priori.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A surgical system for performing laser treatment within a treatment space comprising:
   a. a surgical mechanical arm comprising a plurality of sequentially coupled independently bendable flexible portions and terminating in a laser tool;
   b. a waveguide supplying laser light to said laser tool, where said waveguide follows a contour of said surgical mechanical arm;
   c. circuitry configured, during laser treatment using said surgical system, to:
      i. monitor curvature by receiving data regarding curvature of one or both of:
         said waveguide;
         one or more of said plurality of sequentially coupled independently bendable flexible portions;
      ii. comparing said received data with at least one threshold, wherein said at least one threshold comprises one or more of: a damage threshold, a leakage threshold, a performance threshold; and
      iii. perform at least one action configured to optimize performance of said laser tool based on said received data and on said comparison.

2. The surgical system according to claim 1, wherein said one or more action comprises:
   generating a control signal; and
   sending said control signal to at least one actuator controlling bending of one or more of said plurality of sequentially coupled independently bendable flexible portions.

3. The surgical system according to claim 1, wherein said one or more action comprises:
   adjusting a control signal; and
   sending said control signal to at least one actuator controlling bending of one or more of said plurality of sequentially coupled independently bendable flexible portions.

4. The surgical system according to claim 1, wherein said one or more action comprises activating or deactivating lasing from said laser tool.

5. The surgical system according to claim 1, wherein said system comprises one or more user interface;
   wherein said one or more action comprises issuing an alert to a user through said one or more user interface.

6. The surgical system according to claim 1, wherein said one or more action comprises activating or deactivating movement of said surgical mechanical arms.

7. The surgical system according to claim 1, wherein said data comprises input from at least one sensor, said at least one sensor comprising one or more of:
   one or more input device sensor; and
   one or more sensor configured to measure curvature of one or more axial portion of said waveguide.

8. The surgical system according to claim 1, wherein said surgical mechanical arm comprises:
   a first independently bendable flexible portion;
   a second independently bendable flexible portion coupled to said first flexible portion;
   wherein said waveguide follows a contour of said first independently bendable portion and said second independently bendable portion;
   wherein said receiving comprises receiving data regarding curvature of said first independently bendable portion and said second independently bendable portion.

9. The surgical system according to claim 1, wherein each of said plurality of sequentially coupled independently bendable flexible portions is independently rotatable.

10. The surgical system according to claim 1, wherein said surgical mechanical arm includes a hollow passageway extending along a length of at least a portion of the surgical mechanical arm, said portion having a tubular structure, and said waveguide is housed within said hollow passageway.

11. The surgical system according to claim 1, wherein said surgical mechanical arm comprises an additional tool configured to manipulate tissue.

12. The surgical system according to claim 1, comprising a second surgical mechanical arm comprising a plurality of sequentially coupled independently bendable flexible portions and terminating in a second arm tool configured to manipulate tissue.

13. A method of laser tool control, the laser too being configured for performing laser treatment within a treatment space, said method comprising, during said laser treatment, using said laser tool for:
   receiving data regarding curvature of one or more axial portion of a laser cable supplying laser light to a laser tool;
   comparing said received data with at least one threshold, wherein said at least one threshold comprises one or more of: a damage threshold, a leakage threshold, a performance threshold; and
   performing at least one action configured to optimize performance of said laser tool, based on said received data and on said comparison.

14. The method according to claim 13, wherein said receiving data regarding a leakage of said laser light comprises receiving said data from one or more sensors connected to said waveguide.

15. The surgical system according to claim 1, wherein said data regarding a leakage of said laser light is received from one or more sensors connected to said waveguide.

16. A method of laser treatment comprising:
   directing a laser tool to a region of a treatment site including at least one treatment area while monitoring curvature of one or more axial portion of a laser waveguide supplying laser light to said laser tool;
   orientating said laser tool so that laser light is directed towards said at least one treatment area; and
   lasing using said laser tool, while, during operation of said laser tool:
   i. monitoring curvature by receiving data regarding curvature of one or more axial portion of said laser waveguide;
   ii. comparing said received data with at least one threshold, wherein said at least one threshold comprises one or more of: a damage threshold, a leakage threshold, a performance threshold; and
   performing and action to optimize performance of said laser tool based on received data from said monitoring, and on said comparison.

17. The method according to claim 16, wherein said laser waveguide follows a contour of at least a portion of a surgical mechanical arm.

18. The method according to claim 17, wherein said monitoring comprises monitoring curvature of one or more axial portion of said surgical mechanical arm.

19. The method according to claim 18, wherein said monitoring comprises using control signals for movement of said surgical mechanical arm.

20. The method according to claim 16, wherein said orientating comprises retroflexing said surgical mechanical arm.

* * * * *